(12) United States Patent
Day et al.

(10) Patent No.: US 10,783,992 B1
(45) Date of Patent: Sep. 22, 2020

(54) INTERACTIVE CROSS-PROVIDER HEALTH CARE PRESENTATION AND MODIFICATION SYSTEM

(71) Applicant: HSTechnology Solutions, Inc., Laguna Hills, CA (US)

(72) Inventors: Edward Day, Glenbrook, NV (US); Ryan Day, Laguna Hills, CA (US); Edward Sicard, Laguna Hills, CA (US); Sylwester Wyrzykowski, Laguna Hills, CA (US)

(73) Assignee: HSTECHNOLOGY SOLUTIONS, INC., Laguna Hills, CA (US)

( * ) Notice: Subject to any disclaimer, the term of this patent is extended or adjusted under 35 U.S.C. 154(b) by 0 days.

(21) Appl. No.: 16/657,762

(22) Filed: Oct. 18, 2019

Related U.S. Application Data

(60) Provisional application No. 62/850,419, filed on May 20, 2019.

(51) Int. Cl.
*G16H 40/20* (2018.01)
*G06Q 30/02* (2012.01)
*G06F 3/0481* (2013.01)
*G06F 3/0484* (2013.01)

(52) U.S. Cl.
CPC .......... *G16H 40/20* (2018.01); *G06F 3/0481* (2013.01); *G06F 3/04847* (2013.01); *G06Q 30/0205* (2013.01); *G06Q 30/0206* (2013.01)

(58) Field of Classification Search
CPC .............. G06F 3/0481; G06F 3/04847; G06Q 30/0205; G06Q 30/0206
See application file for complete search history.

(56) References Cited

U.S. PATENT DOCUMENTS

| 2009/0043801 | A1* | 2/2009 | LeClair | .................. G06Q 40/08 |
| 2012/0284138 | A1* | 11/2012 | Shave | ................ G06Q 30/0207 705/26.3 |
| 2014/0039911 | A1* | 2/2014 | Iyer | ........................ G06Q 50/22 705/2 |
| 2018/0268320 | A1* | 9/2018 | Shekhar | ................ G06F 19/328 |

* cited by examiner

Primary Examiner — Evangeline Barr
(74) Attorney, Agent, or Firm — Knobbe, Martens, Olson & Bear, LLP

(57) ABSTRACT

A cross-provider health care system is provided to analyze provider health care determinations with respect to a baseline and present interactive controls for modification of the determinations. Interactive maps are provided for presenting and interacting with health care provider characteristics.

20 Claims, 11 Drawing Sheets

INTERACTIVE CROSS-PROVIDER HEALTH CARE PRESENTATION AND MODIFICATION SYSTEM

CROSS-REFERENCE TO RELATED APPLICATION

The present application claims priority to U.S. Provisional Patent Application No. 62/850,419, filed on May 20, 2019, which is incorporated by reference herein.

BACKGROUND

Computing devices may be used to provide services in a network environment. For example, a computing device may provide a data file, such as a health care data file, to a computing service provider via a network, such as the internet. The computing service provider may include one or more computing devices that process the data file. Processing the data file may include determining health care claims, storing health care-related data, and the like.

SUMMARY

The following presents a simplified summary of one or more aspects in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later. One aspect includes systems and/or methods that provide features for a health care processing system. The features include generating a network resource configured to cause a computing device to display a graphical user interface comprising: a health care data overview portion configured to present a baseline amount for a health care service represented by a health care data record; a real-time adjustment detail portion configured to present a result of adjusting health care data regarding the health care service in substantially real-time; and an interactive adjustment control, wherein a user interaction with the interactive adjustment control causes a change to an adjustment factor applied to the health care data, and wherein the real-time adjustment detail portion automatically updates presentation of the result of adjusting the health care data using the changed adjustment factor in response to user interaction with the interactive adjustment control; and sending the network resource to the computing device. Another aspect includes systems and/or methods that provide features for a health care processing system. The features include generating a network resource configured to cause a computing device to display a graphical user interface comprising: a map of a geographic area in which a first health care service provider is located; a first object representing a location of the first health care service provider within the geographic area, wherein a visual property of the first object represents a classification to which the first health care service provider is assigned based on historical experience processing health care data records associated with the first health care service provider; and a second object representing a location of the second health care service provider within the geographic area, wherein a visual property of the second object represents a classification to which the second health care service provider is assigned based on historical experience processing health care data records associated with the second health care service provider; and sending the network resource to the computing device.

BRIEF DESCRIPTION OF THE DRAWINGS

Throughout the drawings, reference numbers may be re-used to indicate correspondence between referenced elements. The drawings are provided to illustrate example embodiments described herein and are not intended to limit the scope of the disclosure.

DETAILED DESCRIPTION OF ILLUSTRATIVE EMBODIMENTS

Figure 1:
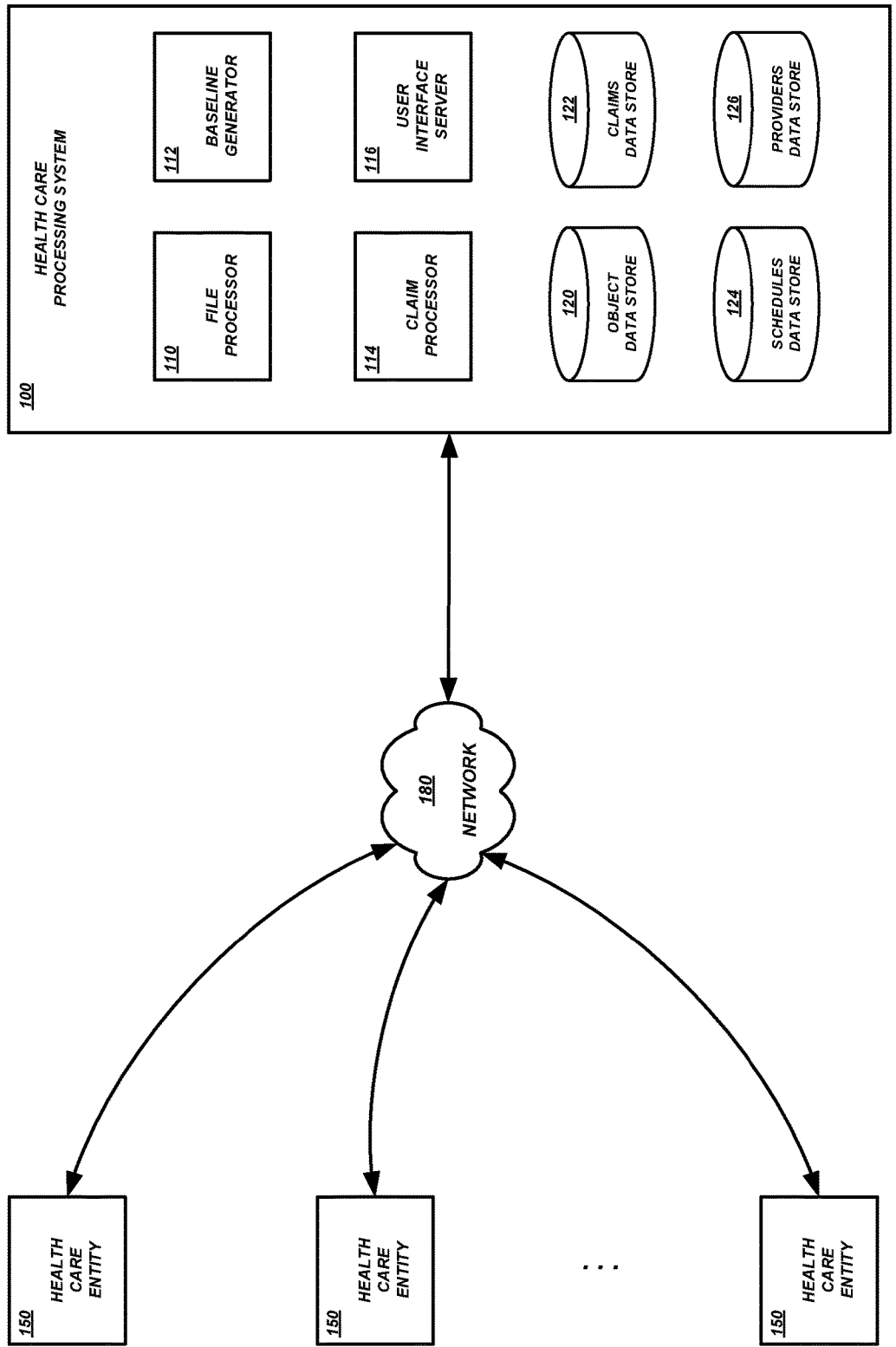
FIG. 1 is a block diagram of an illustrative computing environment including a health care processing system and multiple health care data entities according to some embodiments.

The present disclosure is directed to augmenting health care data with additional data for use in processing health care claims, and to dynamic user interfaces for viewing, modifying, and otherwise interacting with health care data. A health care processing system may provide network-accessible services for determining health care service eligibility and processing health care claims. The health care processing system can process and augment health care data with additional data generated using selectively-applied data transformations, dynamically-determined augmentation algorithms, and the like. The health care processing system can provide graphical views of health care data. For example, the health care processing system can generate interactive maps showing health care provider locations with visual properties indicating various metrics, interactive adjustment controls to see the effect of adjustments to health care data in real time, etc.

Conventional systems for processing health care data are associated with a number of costs, inefficiencies, and drawbacks. For example, conventional systems require the negotiation of comprehensive rate tables for all covered services, and re-negotiation on a periodic (e.g., annual) basis. As another example, conventional systems present health care information in ways (e.g., static reports, include pages of numbers and tables, etc.) that are not dynamic and user friendly. As yet another example, conventional systems fail to provide real-time information about both the quality and financial impact of health care. These and other shortcomings of conventional systems make it difficult—if not impossible from a practical standpoint—for health care consumers, providers, and managers to make fully informed choices about where health care is most efficiently and effectively provided.

With reference to one illustrative shortcoming of conventional systems, the task of navigating a large electronic catalog of items (e.g., a catalog with hundreds or thousands of items, corresponding to individual providers or services) to locate items of interest can be burdensome and time consuming for users, especially if the users do not know the names or generic descriptors of the desired items. In some instances, a user can locate items by navigating a browse structure (e.g., a "browse tree") in which the items are arranged by category and subcategory. Typically, however, the browse tree includes several levels of categories, requiring the user to navigate through several levels of browse nodes or category pages to arrive at the subcategory of interest. Further, in many cases, the items of interest are not accurately or intuitively categorized, requiring the user to perform additional navigation or keyword searching. Thus, the user frequently has to perform numerous navigational steps to arrive at the "detail page" of interest. Classification algorithms and user interfaces of the type disclosed herein significantly reduce this problem, allowing users to locate items of interest with fewer steps. For example, in the embodiments described herein, when the user is to be presented with one or more items, each item is represented by an object that includes a visual property indicative of a property of the item. The object may also include or be associated with an additional interface or display component representing additional properties or other information associated with item, allowing the user to easily obtain desired information. Each such object thus serves as a programmatically selected shortcut to the item's description, allowing the user to bypass traditional navigational structures (e.g., browse trees). Beneficially, programmatically identifying items of interest and presenting the user with dynamic, interactive objects representing these items improves the speed and efficiency of the user's navigation through the electronic catalog by reducing or eliminating the need for the user to perform navigation and/or search actions to locate such items. This can be particularly true for computing devices with small screens, where fewer items can be displayed to the user at a time and thus navigation of larger volumes of items is more difficult.

With reference to another illustrative shortcoming of conventional systems, the task of processing health care claim data often relies upon comprehensive rate tables for all covered services. The determination of rate information within the rate tables is typically a manual process requiring human intervention and re-negotiation on a periodic (e.g., annual) basis. In many cases, services that are part of a particular health care claim are associated with variable context-specific factors. In some cases, services that are part of a particular health care claim are rare, are customized for particular consumer or provider, or are indicated using non-standard identifiers or other associated data. In these and other cases, the services are not accurately reflected (or not reflected at all) in the rate tables. Thus, a user frequently has to perform manual steps to process such health care claims, and the result may be inaccurate, subjective, or otherwise not adequately supported. Baseline processing and augmentation algorithms described herein significantly reduce this problem, allowing computing systems to automatically process health care claim data in a consistent manner and without continued user intervention typically required to maintain rates and deal with cases not covered by the maintained rates. Beneficially, the systems and algorithms described herein replace the largely manual process by using baselines and augmenting both the results produced by applying baselines and also the data that is to be output from the system. The augmentation is applied according to rules that remove the subjective determinations that typically result from manual intervention, and also automatically deal with rare cases, variable cases, and non-standard data. This can be particularly beneficial in high-volume and/or cross-provider health care data processing.

Aspects of the present disclosure address, among other things, issues with health care data processing such as those discussed above. More specifically, a cloud-based health care processing system is disclosed. The health care processing system obtains, from multiple disparate sources, data regarding health care that has been provided—or will be provided—in any number of disparate locations. The health care processing system ingests the health care data, and processes it into a structured, hierarchical form that can be augmented with additional information. The health care processing system can perform a number of different processes, including: identifying data for particular health care procedures and other services; transforming the data into a different format for more efficient processing; determining eligibility and valuation of the health care services with respect to one or more standards or other baselines; dynamically selecting and executing augmentation algorithms using baseline valuations; and generating health care augmentation data. The health care processing system can then augment the structured, hierarchical health care data with the health care augmentation data, and provide output back to the sources of the health care data. In this way, the health care processing system can provide automated standards-based valuation and other processing of health care data, thus streamlining the processing of health care data and reducing the overall cost of health care services.

Additional aspects of the present disclosure relate to providing dynamic, interactive, graphical views of the health care data that provide, among other things, a solution to issues with viewing and interacting with health care data such as those discussed above. In some embodiments interactive maps are generated, showing health care provider locations with visual properties indicating various metrics. Such maps allow users to visually compare providers within a geographic area based on differences in the represented metrics. For example, the metrics may relate to the likelihood of accepting standards-based valuation of health care, the degree to which providers charge more than a baseline valuation, etc. In some embodiments, interactive adjustment controls allow users to see the effect of adjustments to health care data processing in real time. For example, users can see the results of applying different adjustment factors to baseline values, augmented values, provider costs, or the like. By providing such dynamic interfaces to users, the health care processing system can allow more efficient and effective decision making with respect to health care.

Although aspects of some embodiments described in the disclosure will focus, for the purpose of illustration, on particular examples of data structures, baselines, transformations, algorithms, and graphical interfaces, the examples are illustrative only and are not intended to be limiting. In some embodiments, the techniques described herein may be applied to additional or alternative data structures, baselines, transformations, algorithms, and graphical interfaces. Various aspects of the disclosure will now be described with regard to certain examples and embodiments, which are intended to illustrate but not limit the disclosure.

Network-Based Health Care Environment

With reference to an illustrative embodiment, FIG. 1 shows an example network environment in which aspects of the present disclosure may be implemented. As shown, the network environment may include a health care processing system 100 and various health care entities 150. The health care processing system 120 and computing devices of the health care entities 150 may communicate with each via one or more communication networks 180. In some embodiments, a communication network 180 (also referred to simply as a "network") may be a publicly-accessible network of linked networks, possibly operated by various distinct parties, such as the internet. In some embodiments, the network 180 may be or include a local area network ("LAN"), wide area network ("WAN"), global area network ("GAN"), or some combination thereof, any or all of which may or may not have access to and/or from the internet.

Generally described, a health care entity 150 may be any of a variety of parties associated with health care services, including consumers, providers, third-party administrators, and the like. For example, a provider of health care services may generate health care data, such as data regarding invoices for services rendered to health care consumers. The health care service provider (also referred to as a "health care provider" or simply as a "provider") may provide the health care data to the health care processing system 100 for payment, authorization, etc. As another example, a consumer of health care services may generate a claim for reimbursement for health care services received, or submit an invoice received from a health care service provider. The health care service consumer (also referred to as a "health care consumer" or simply as a "consumer") may provide claim data to the health care processing system 100. As yet another example, a third-party administrator may handle any number of claims from any number of providers and/or associated with any number of consumers. The third-party administrator can generate health care data regarding the claims and provide the health care data to the health care processing system 100. In these and other examples, the entity 150 may include one or more computing devices (e.g., servers, desktop computers, etc.) configured to transmit health care data to the health care processing system 100 and/or receive augmented health care data from the health care processing system 100.

Health care processing system 100 may comprise a plurality of components. In some embodiments, health care processing system 100 comprises a file processor 110 to process files of health care data received from a health care entity 150, generate structured representations of the files, augment data in the structured representations, generate augmented files for transmission back to health care entities 150, and the like. Health care processing system 100 may also include one or more baseline generators 112 to analyze health care data with respect to standards or other baselines to determine eligibility, pricing, and the like. Health care processing system 100 may also include one or more claim processors 114 to manage processing of health care claims, including using results of analysis performed by the baseline generators 112. Health care processing system 100 may also include a user interface ("UI") server 116 to generate user interfaces (e.g., web pages, mobile application display data, etc.), process user interactions with the UIs, and the like.

Health care processing system 100 may also include various data store components to store health care data, data used to process health care data, data generated when processing health care data, and the like. In some embodiments, health care processing system 100 may include an object data store 120 to store data files received from health care entities 150, files generated to send to health care entities 150, etc. Health care processing system 100 may also include a claims data store 124 to store data regarding health care claims being process and/or previously processed. Health care processing system 100 may also include a schedules data store 124 to store data regarding valuation schedules and other data used to process health care claims. Health care processing system 100 may also include a providers data store 126 to store data regarding health care service providers, such as data regarding propensity to accept or reject standards-based pricing, data regarding costs incurred by providers when providing health care services, etc.

Individual components of the health care processing system 100 may be implemented one or more computing devices. For example, each component may be implemented on a separate computing device, or separate set of computing devices. As another example, a single computing device or set of computing devices may be shared among multiple components. In some embodiments, the features and services provided by the health care processing system 100 may be provided by one or more virtual machines implemented in a hosted computing environment. The hosted computing environment may include one or more rapidly provisioned and released computing resources, such as computing devices, networking devices, and/or storage devices. A hosted computing environment may also be referred to as a "cloud" computing environment.

While the example of FIG. 1 displays a limited set of example health care entities 150, it will be appreciated that other arrangements may exist in other embodiments. For example, a single health care processing system 100 may communicate with any number of health care entities 150. As another example, there may be multiple health care processing systems 100. In this example, a single health care entity 150 may communicate with multiple health care processing systems 100, or individual health care entities 150 may be assigned to individual health care processing system 100.

Health Care Data Processing and Augmentation

Figure 2:
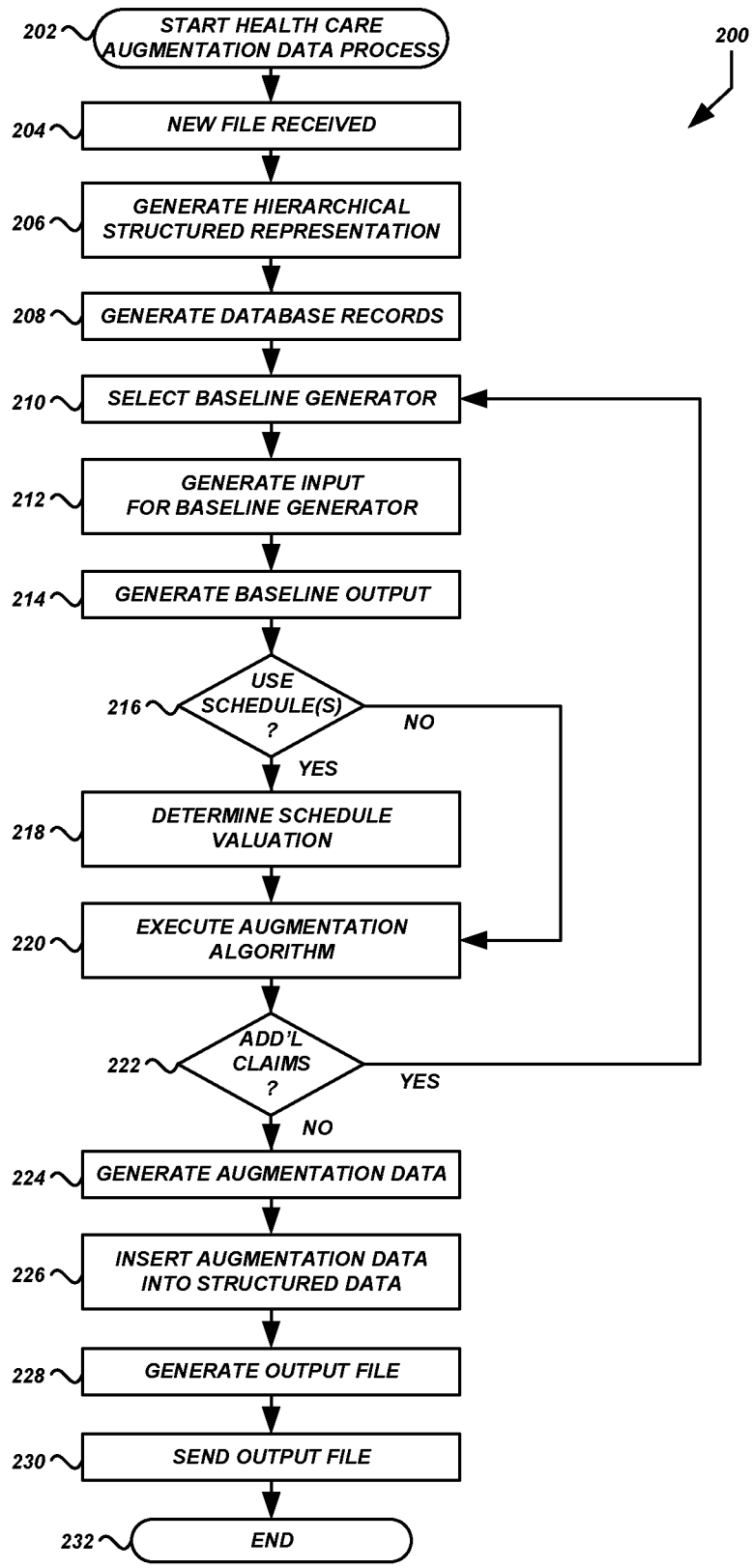
FIG. 2 is a flow diagram of an illustrative routine for processing and augmenting health care data according to some embodiments.

FIG. 2 is a flow diagram of an example routine 200 executed by the health care processing system 100 to process and augment health care data received from a health care entity. Routine 200 will be described below with additional reference to FIG. 3, which shows example processing of—and augmentation to—a health care data file.

Figure 11:
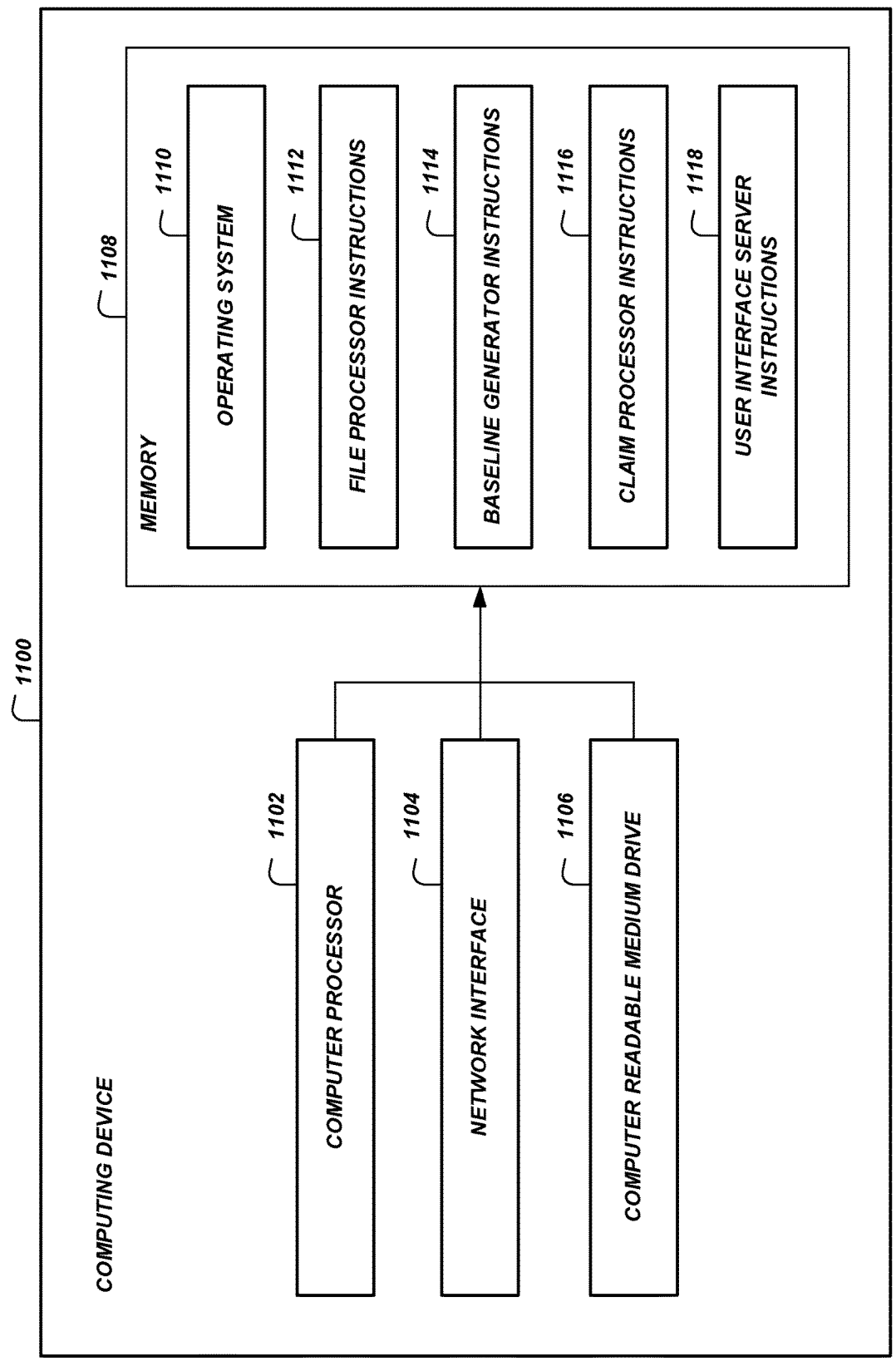
FIG. 11 is a block diagram of an illustrative computing system configured to implement features of the present disclosure according to some embodiments.

Routine 200 begins at block 202. Routine 200 may begin in response to an event, such as when the health care processing system 100 is initialized, when the health care processing system 100 opens a connection with a health care entity 150, etc. In some embodiments, routine 200 may be executed according to a predetermined or dynamically determined schedule. When routine 200 is initiated, a set of executable program instructions stored on one or more non-transitory computer-readable media (e.g., hard drive, flash memory, removable media, etc.) may be loaded into memory (e.g., random access memory or "RAM") of computing device. For example, as shown in FIG. 11, file processor instructions 1112, baseline generator 1114, and/or claim processor instructions 1116 may be loaded into memory 1108 of one or more health care processing system computing devices 1100 and executed by one or more processors 1102. In some embodiments, routine 200 or portions thereof may be implemented on multiple processors (on the same or separate computing devices), serially or in parallel.

At block 204, the health care processing system 100 may receive a health care data file from a health care entity 150. The health care data file may include one or more records regarding health care services that have been—or may be—performed. Illustratively, the health care entity 150 may be a third-party administrator ("TPA"), and may provide a file of one or more records regarding claims that have been (or will be) paid by the TPA to one or more health care providers. The health care processing system 100 may store the health care data file in the object data store 120, where it is accessible to various components of the health care processing system 100. For example, the health care data file may be accessed by the file processor 110.

Figure 3:
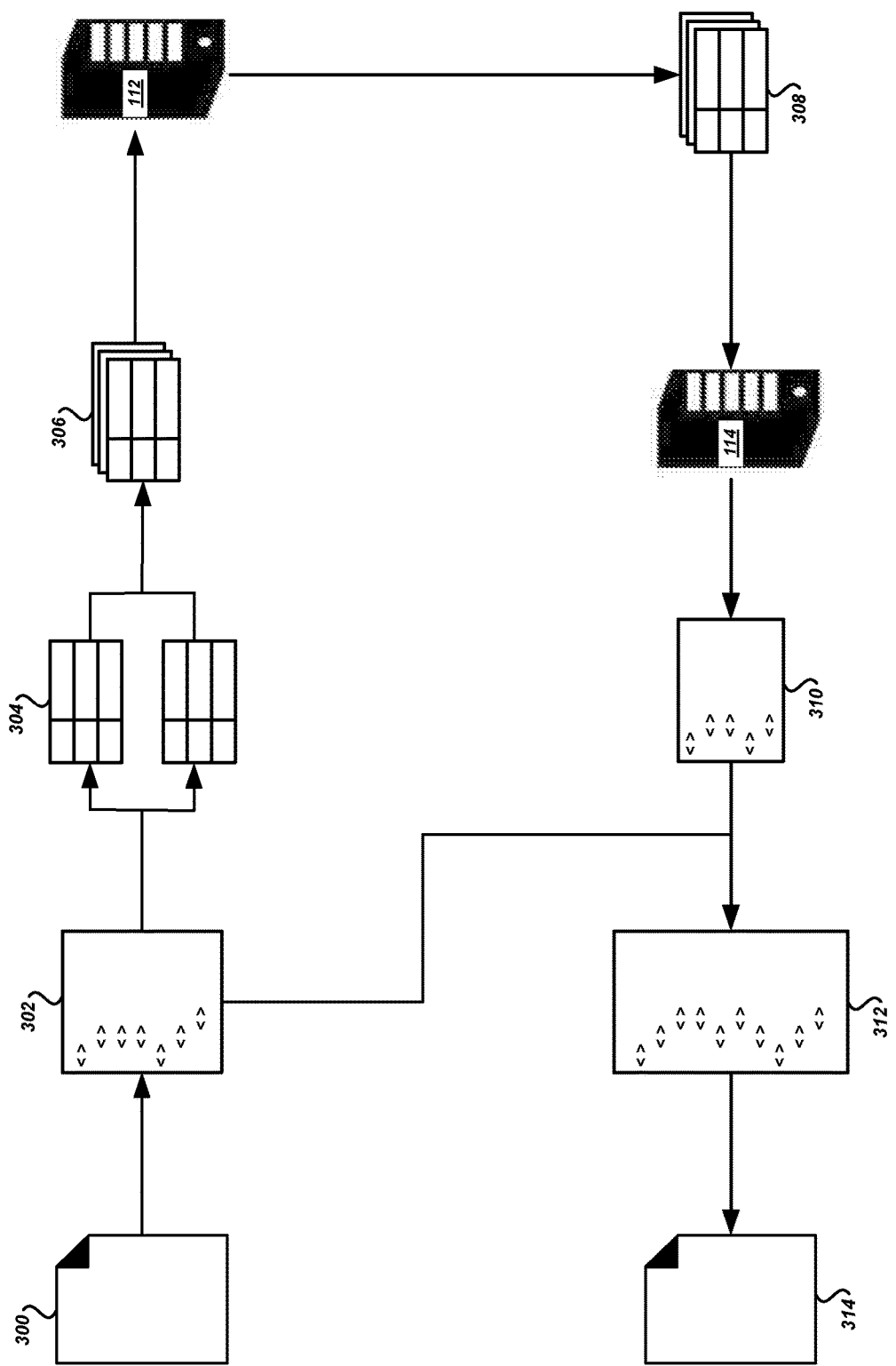
FIG. 3 is a diagram of illustrative health care data flows and transformations to health care data according to some embodiments.

At block 206, the file processor 110 or some other component of the health care processing system 100 may generate a structured representation of the data in the health care data file for processing. The file processor 110 may generate a hierarchical structured representation using an eXtensible Markup Language ("XML") format, JavaScript Object Notation ("JSON") format, or some other format for hierarchical structured data. FIG. 3 shows an example health care data file 300 transformed into a hierarchical structured representation 302 of the health care data within the health care data file 300. As shown, the health care data file 300 may be a series of records in the format of a "flat" data file. For example, the health care data file 300 may be in the form of a comma separated value ("CSV") file, a tab delimited text file, etc. The file processor 110 may read the records of the health care data file 300 and generate sets of nodes, wherein individual nodes have properties, and wherein individual nodes relate to other nodes according to a hierarchical structure (e.g., some nodes are parent nodes, some nodes are child nodes, some nodes are both parent nodes and child nodes, etc.). For example, a particular consumer or provider may be associated with multiple individual data records in the health care data file 300. A node may be created representing consumer or provider, and multiple child nodes may be created representing the individual records. This process may be repeated for each heath care data record or set of records in the health care data file 300 until the hierarchical structured representation 302 includes all information needed to represent the health care data file 300 and recreate the health care data file 300.

At block 208, the file processor 110 or some other component of the health care processing system 100 may generate database records of the health care data from the hierarchical structured representation generated above. As shown in FIG. 3, the hierarchical structured representation 302 can be processed into relational database records 304. Generating database records, such as records in tables of a relational database, can improve the efficiency and ease of processing the health care data. For example, rather than reading and manipulating a hierarchical structured representation 302 (whether in memory or persistent storage), working with relational database records 304 may provide certain processing and design advantages, such as the ease with which relational data may be queried and analyzed.

In some embodiments, the hierarchical representation 302 may first be processed to generate intermediate database records in one or more staging tables. The intermediate database records may represent an intermediate step between the hierarchical representation 302 and the relational database records 304. For example, individual portions of the hierarchical representation 302 may be mapped to one or more database tables. While the file processor 110 traverses individual portions of the hierarchical representation 302, the file processor 110 can generate corresponding intermediate records to be stored in the tables. Once the hierarchical representation 302 has been stored in the staging tables (or in parallel with storing the hierarchical representation 302 in staging tables), the data can be transformed into relational database records and stored in relational database records 304 for subsequent processing as described in greater detail below. While staging tables may correspond closely to the hierarchical representation 302, the relational database records 304 may correspond to the format and structure used by subsequent processes.

At block 210, the health care processing system 100 may select a baseline generator 112 to process health care data (e.g., a claim represented by records in the relational database tables) with respect to a particular baseline. As described above, there may have been multiple claims represented by the health care data in the health care data file 300. Thus, there may be records in the relational database records 304 that represent multiple claims. Baseline generators 112 may be selected to process claims in a predetermined or dynamically-determined order, such as in chronological order of the claims (e.g., service date, bill date, etc.), in the order in which the records appear in the relational database records 304, in a random order, etc. A baseline generator 112 may be a component that processes a health care data record and determines various criteria for the claim (e.g., whether the claim eligible), generates initial augmentation data for the claim, such as a valuation according to a particular standard (e.g., Medicare) or other baseline, etc. The baseline generator 112 may implement an algorithm for determining eligibility and/or valuation for the claim according to the corresponding baseline and/or type of claim.

The particular baseline generator 112 for a given claim may be selected based on one or more properties of the claim, as indicated by one or more health care data records representing the claim, such as data in the relational database records 304. For example, if data indicates the claim is an inpatient hospital claim, one baseline generator 112 may be used, while if the claim is a physician claim, a different baseline generator 112 may be used. In some embodiments, the set of baseline generators 112 may include generators for one or more of: an outpatient baseline, an inpatient baseline, an ambulatory baseline, a physician baseline, a dialysis baseline, a hospice baseline, another baseline, some combination thereof, etc. Any or all of the separate baseline generators 112 may take the same or different input, use the same or a different algorithm, and/or generate the same or different output as any other baseline generator 112.

At block 212, the health care processing system 100 can generate input data for the selected baseline generator 112. As shown in FIG. 3, the health care processing system 100 can read data from the relational database records 304 for the current claim, and generate baseline generator input data 306 for processing by the selected baseline generator 112. The baseline generator input data 306 may be the same for each baseline generator 112, or individual baseline generators 112 may be configured to process different sets, combinations, and/or formats of input data.

In one specific, non-limiting embodiment, the baseline generator input data 306 may include various parameters regarding the claim, such as identifiers of the provider, date(s) of service, etc. The baseline generator input data 306 may also include a set of fixed-format, fixed-length records (e.g., a string of 200-byte records) with details of the claim. The set of records may include a record for high-level claim data, such as a patient identifier, date(s) of service, demographic data, and the like. This record may be referred to as the "C" record. The set of records may also or alternatively include a record of diagnosis identifiers, such as standardized codes, that apply to the entire claim and are not specific to any line item. The diagnosis codes may be of a particular form (e.g., ICD-9-CM), and there may be a maximum number of such codes in the record (e.g., a maximum of 16). This record may be referred to as the "D" record. The set of records may also or alternatively include one or more additional records of diagnosis identifiers, such as additional diagnosis codes of the same form as the "D" record (e.g., when there are more than the maximum number for the claim), diagnosis codes of a different form (e.g., ICD-10-CM), or the like. This record may be referred to as the "E" record. The set of records may also or alternatively include a record for adjustments (e.g., value codes, amounts, etc.), and there may be a maximum number of such codes in the record (e.g., a maximum of 16). This record may be referred to as the "F" record. The set of records may also or alternatively include one or more records for individual line items of the claim. For example, there may be a single line item for each procedure performed in connection with the claim. The line-item-specific records may be referred to as a "L" records, and there may be a maximum number of such records (e.g., a maximum of 450). In some embodiments, certain records may be optional or omitted. For example, the "F" record may be optional. As another example, no "E" record may be used if there is a "D" record, or no "D" record may be used if there is an "E" record.

In some embodiments, the health care processing system 100 may perform additional processing to generate data to be included in the baseline generator input data 306. For example, the health care processing system 100 may determine a composite or "group" that is representative of the claim or portions thereof. Such a group may be referred to as a diagnosis related group or "DRG," and the health care processing system 100 may determine an identifier or "DRG code" indicative of the determined DRG. The parameters used to determine the DRG code may include the patient's date of birth, gender, discharge status, discharge date, one or more diagnosis codes, one or more procedure codes, other data, some combination thereof, etc.

Figure 4:
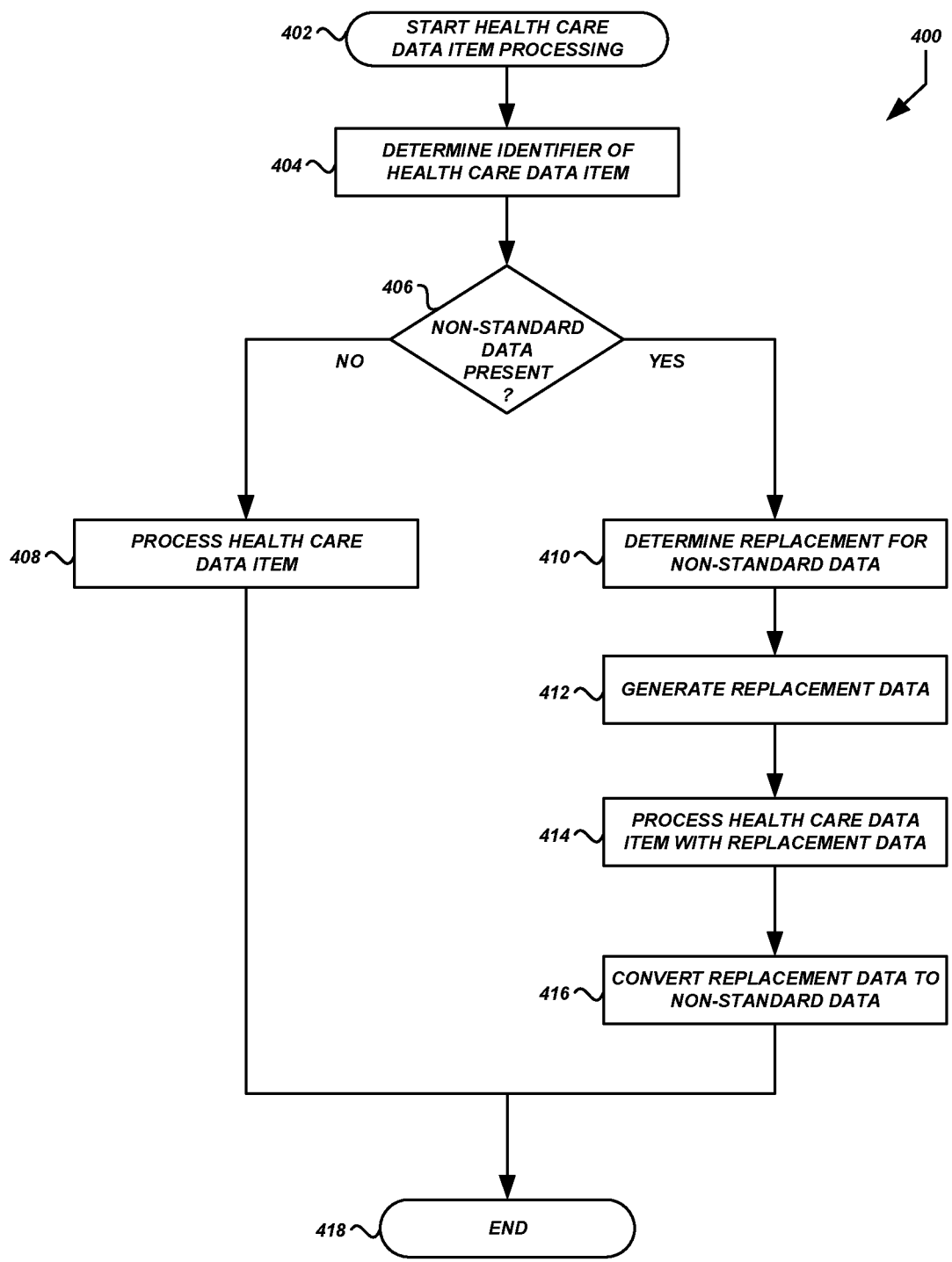
FIG. 4 is a flow diagram of an illustrative routine for processing non-standard items of health care data according to some embodiments.

In some embodiments, particular line items or other aspects of a claim may include non-standard or data. For example, the health care data file 300 may have included a code for a particular line item that is not recognized by the selected baseline generator 112, or the baseline generator 112 is otherwise not configured to process the data. In such cases, the health care processing system 100 may convert, transform, replace, or otherwise process the data into a type or form that will be processed by the baseline generator 112. For example, a line item may be replaced by another line item (e.g., 1-to-1). As another example, a line item may be expanded into multiple line items (e.g., 1-to-many). An example of processing such non-standard data into a form or type that will be processed by the baseline generator 112 is shown in FIG. 4 and described in greater detail below with respect to a routine for processing individual items of health care data.

In some embodiments, a claim may be linked to a previous claim. For example, a consumer may receive an invoice from a provider for a remaining balance of an invoice that the provider previously submitted (or that was submitted on the provider's behalf) to the health care processing system 100. In this case, the health care processing system 100 may link the current claim for the remaining balance to the original claim using, e.g., an identifier of the original claim or other linking data. In this way, the health care processing system 100 can access the prior claim to ensure that a valuation, eligibility, or the like is not determined based solely on the new claim, but is rather properly considered based on the new claim in combination with the prior claim.

The example records and other aspects of the baseline generator input data 306 are provided for illustrative purposes only, and are not intended to be exhaustive, limiting, or required in all embodiments.

At block 214, the selected baseline generator 112 or some other component of the health care processing system 100 may process the baseline generator input data and generate baseline data that represents properties of the claims, such as baseline valuation, eligibility, any additional processing required, errors, and the like. The baseline generator input data may be provided to the selected baseline generator 112 as a parameter to a procedure call, as a data structure in volatile or persistent memory, or the like. The baseline generator 112 may then process the baseline generator input data according to the algorithm and current state of the baseline generator 112 (e.g., using the current rates or other calculation data for the baseline). The baseline data may represent the valuation that has been authorized for the claim and/or individual line items, the eligibility (or lack thereof) for the claim and/or individual line items, whether the claim or individual line items could not be processed even though they may be eligible, etc. For example, if the baseline to be used is the valuation authorized by a particular standard or schedule (e.g., Medicare for outpatient claims), the baseline generator 112 may generate output that reflects the authorized valuation (if available) for the claim and/or individual line items. Illustratively, the valuations may be computed as the sum of the relevant Medicare reimbursement amount, applicable deductible amount, adjusted/reduced coinsurance amount, and miscellaneous adjustments (e.g., blood deductible amount).

In one specific, non-limiting embodiment, the baseline data 308 may be a set of fixed-format, fixed-length records (e.g., a string of 200-byte records). The set of records may include one or more records of modifications or "edits" to the claim. These records may be referred to as "M" and/or "N" records. In such records, there may be a maximum number of individual edits in a single record. The set of records may include one or more records of modifications or "edits" to the diagnoses. These records may be referred to as "O" and/or "P" records. In such records, there may be a maximum number of individual diagnosis edits in a single record (e.g., a maximum of 5). The set of records may include one or more records of modifications or "edits" to the line items. These records may be referred to as "R" and/or "S" records. There may be a pair of "R" and "S" records for each line item of the claim (e.g., a pair of "R" and "S" records for each "L" record in the baseline generator input data 306). The "R" records may indicate certain line item edits to procedures, while "S" records may include data representing dates, revenue codes, additional edits, etc.

In another specific, non-limiting embodiment, the baseline data 308 may include records that are in addition to, or alternatives to, the records described above. For example, a set of records for each line item of the claim (e.g., each "L" record) may be generated. The set of records may include a record of data representing line item payment classification data. Such a record may be referred to as a "T" record. The set of records may include a record of data representing line item payment amounts. Such a record may be referred to as a "W" record. Thus, if there are n line items for a particular claim (where n is a positive integer), there may be n corresponding "T" and "W" records. The baseline data 308 may also include a record of data representing the claim-level payment totals for the entire claim. Such a record may be referred to as a "V" record. Illustratively, if there are three (3) line items for a claim, the set of output records may include 1 "V" record, 3 "T" records, and 3 "W" records.

In some embodiments, as shown in FIG. 3, the output data 308 from the baseline generator 112 may include the baseline generator input data 306 in addition to the additional data (e.g., the records described above) generated by the baseline generator. An example routine for processing individual items of health care data is shown in FIG. 4 and described in greater detail below. The example records and other aspects of the baseline data 308 are provided for illustrative purposes only, and are not intended to be exhaustive, limiting, or required in all embodiments At decision block 216, health care processing system 100 can determine whether the baseline data is to be supplemented using one or more schedules. A baseline generator 112 may not be able to determine a valuation for particular elements (e.g., line items) of a claim. In such cases, the baseline generator 112 may indicate, in the baseline data, that a valuation was unable to be determined. In some embodiments, a baseline generator 112 may include in the output record for a particular line item (e.g., in an "R," "S," "T," and/or "W" record) a code indicating that the health care processing system 100 is to refer to a separate valuation schedule to determine the valuation for the line item. For example, a baseline generator 112, such as the processor for outpatient claims, may not be configured to determine valuations for certain line items, such as injections, labs, anesthesia, ambulatory items, durable medical equipment, or the like. When the baseline generator 112 encounters such a line item in a claim, the baseline generator 112 may include a code in the baseline data indicating that for this particular line item, the health care processing system 100 is to obtain the valuation from a separate schedule. If the health care processing system 100 encounters such a code (or other indication that a schedule is to be used), the routine 200 can proceed to block 218. Otherwise, if no schedule is to be used, the routine 200 can proceed to block 220.

At block 218, the health care processing system 100 can access one or more schedules to determine valuations of line items for which the baseline generator 112 did not determine a valuation. For example, if a particular claim was an outpatient claim and included anesthesia, the baseline generator 112 that process the line items for that claim may have included a code, in the baseline data, indicating that the valuation for the anesthesia line item is to be determined using a separate schedule The health care processing system 100 can access the anesthesia schedule, search for identifying information associated with the current line item (e.g., an identifying code), and obtain the valuation for the line item. The health care processing system 100 may then alter the baseline data by including the determined valuation in the record(s) for the current line item. This process may be repeated, as needed, for any other such line items in the baseline data.

Figure 5:
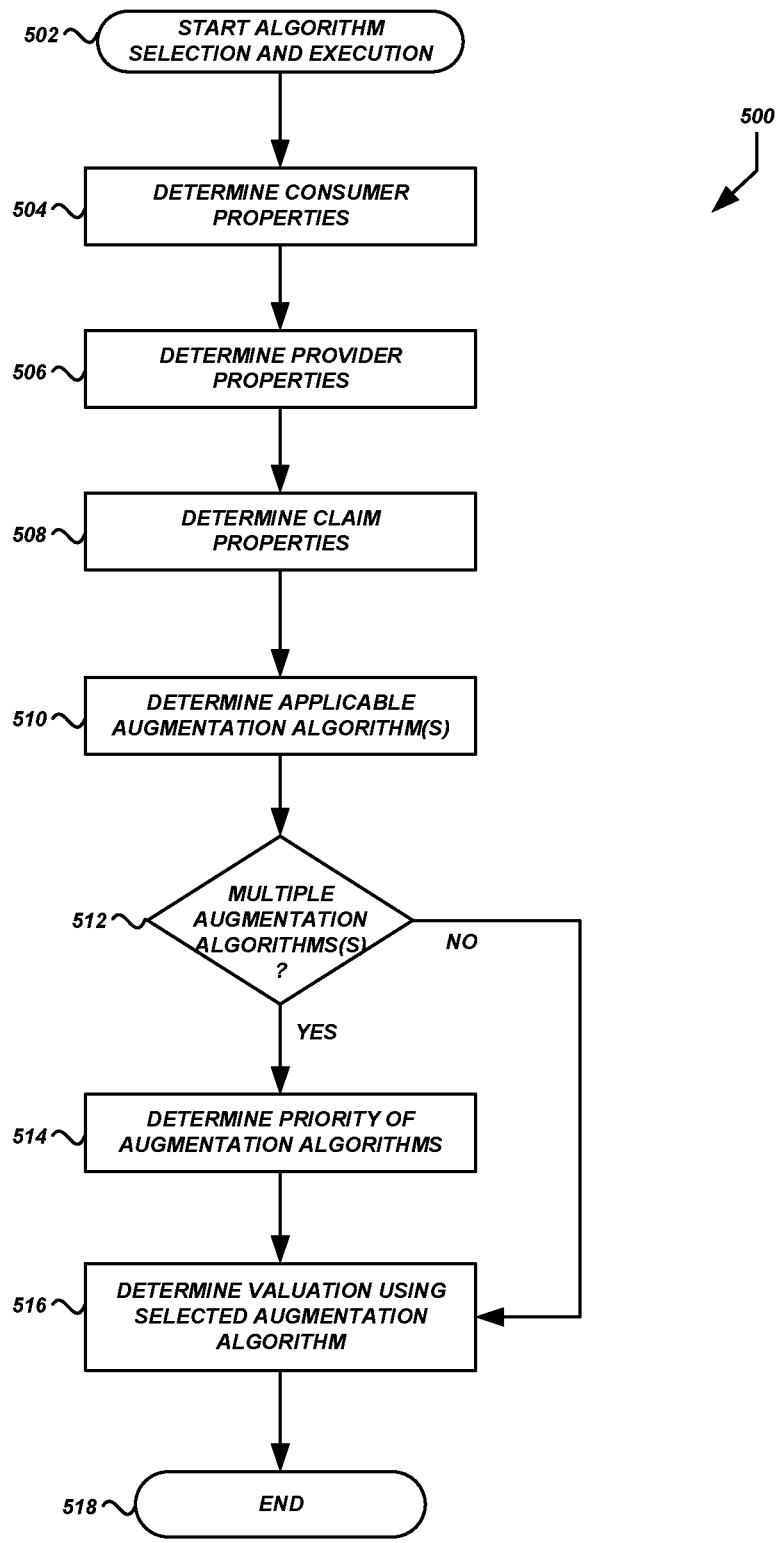
FIG. 5 is a flow diagram of an illustrative routine for processing health care data using selectively-applied augmentation algorithms according to some embodiments.

At block 220, the health care processing system 100 can process the baseline data using a claim processor 114. The claim processor 114 can determine various data to be included in health care augmentation data that will be generated in subsequent blocks of the routine 200. The data may include, e.g., a permitted or authorized valuation for the claim and/or any of its component line items. The particular valuation may be determined based on the initial valuation determined by the baseline generator 112, but may not necessarily be the same as the valuation determined by the baseline generator 112. For example, the baseline generator 112 may determine the Medicare valuation for a claim and its component line items. Additional valuation information may or may not be determined using separate schedules, as described above. However, the valuation information determined at these blocks may be a starting point for the final valuation determined by the claim processor 114. The health care processing system 100 may choose a claim processor 114 based on certain information associated with the claim (e.g., provider, patient, service type, etc.). As shown in FIG. 3, the determined claim processor 114 can process the baseline data 308 to determine valuation data that will be output by the health care processing system 100. An example routine for selecting and using a claim processor 114 to process baseline data is shown in FIG. 5 and described in greater detail below.

At decision block 222, the health care processing system 100 can determine whether there is data in the relational database records 304 representing an additional claim or claims to be processed. For example, when processing the current claim as described above, or when finished generating augmentation data for the claim, the health care processing system 100 can mark the claim as processed. The health care processing system 100 can determine, at decision block 222, whether there are claims that have not been marked as processed. If there are unprocessed claims, the routine 200 can return to block 210. Otherwise, if there are not claims remaining to be processed, the routine 200 can proceed to block 224.

At block 224, the health care processing system 100 can generate health care augmentation data 310 representing the processed claims, shown in FIG. 3. In some embodiments, the health care augmentation data 310 may be or include records that indicate the valuation(s) determined by the claim processor(s) 114 for the claim(s). Illustratively, the health care augmentation data 310 for a particular claim may include eligibility data, valuation data, and/or other data related to the claim and/or individual line items. The health care processing system 100 may generate the health care augmentation data 310 in a format that is compatible with the health care data that the health care augmentation data is augmenting. For example, the health care augmentation data 310 may be generated in a format that is easily merged into, or otherwise compatible with, the hierarchical structured representation 302, the health care data file 300, etc. In one specific non-limiting embodiment, the health care augmentation data 310 may be generated as a collection of nodes in a hierarchical structured format (such as XML). Each claim may be represented by one or more top-level nodes and corresponding child nodes, wherein the child nodes represent the line items of the claim. For example, the health care augmentation data 310 for a particular claim may include nodes for: valuation methodology, allowed amounts, saving amounts, organization identifiers, per diem or flat rate amounts, rejection reasons/codes, other data, or some combination thereof. The health care augmentation data 310 for a particular line item may include nodes for: valuation methodology, monetary amounts, reference identifiers, rejection reasons/codes, adjustments, other data, or some combination thereof.

At block 226, the health care processing system 100 can use the health care augmentation data 310 generated above to generate augmented health care data 312, shown in FIG. 3. The health care data to be augmented may be the hierarchical structured representation 302. The health care processing system 100 may retain the hierarchical structured representation 302 in memory during processing of the claims. In some embodiments, the health care processing system may serialize the hierarchical structured representation during processing of the claims and then deserialize it for augmentation, regenerate the hierarchical structured representation 302 from the health care data file 300 or relational database records 304, or otherwise obtain the hierarchical structured representation 302. With the hierarchical structured representation 302 available (e.g., in volatile memory of a computing device), the health care processing system 100 can manipulate the representation to insert health care augmentation data 310.

In an illustrative embodiment, the health care processing system 100 may traverse the health care augmentation data element-by-element to identify claims, and then identify the corresponding element (e.g., node) in the hierarchical structured representation 302. The health care processing system 100 may then insert the element(s) from the health care augmentation data into the hierarchical structured representation 302 at the appropriate location. Insertion may be accomplished by creating a child node, sibling node, or node group for the health care augmentation data. This process may be repeated, as needed, for each remaining element in the health care augmentation data. In some embodiments, the health care processing system 100 may traverse the hierarchical structured representation 302 and, for each element (e.g., node) corresponding to a claim or line item, determine whether there is a corresponding element in the health care augmentation data to insert into the hierarchical structured representation 302.

At block 228, the health care processing system 100 can use the augmented health care data 312 to generate a health care processing system output file 314, shown in FIG. 3. The health care processing system 100 may generate the separate output file 314 when, e.g., the entity that is to receive output of the health care processing system 100 is not configured to receive the type, structure, and/or format of augmented health care data 312 generated internally. For example, the file processor 110 can generate an output file that is in the same format—or substantially the same format—as the health care data file 300.

At block 230 the health care processing system 100 can send the health care processing system output file 314 to an entity outside the health care processing system 100. For example, the health care processing system 100 may send the output file 314 to the health care entity 150 from which the health care data file 300 was received.

At block 232, routine 200 may end. Although the blocks of FIG. 2 are shown and described as occurring sequentially, in some embodiments certain blocks may be performed in a different order, in parallel, asynchronously, repetitively, etc. For example, multiple subroutines each including blocks 210, 212, 214, 216, 218, and 220 (or a subset thereof) may be performed concurrently to process claim data. In each subroutine, or in each iteration of the routine 200, the same or different baseline generators 114 and/or claim processors 114 may be selected and used, depending upon the specific properties of the claim being processed. In some embodiments, some blocks may be omitted. For example, blocks 206 and/or 208 may be omitted, depending upon the particular data format that the health care processing system 100 is configured to process using baseline generators 112, claim processors 114, etc.

FIG. 4 is a flow diagram of an example routine 400 executed by the health care processing system 100 to process individual items of health care data. The example routine 400 includes the transformation of non-standard health care data into a type or form able to be processed by the selected baseline generator 112, and then back into the non-standard form in which it was originally obtained.

Routine 400 begins at block 402. Routine 400 may begin in response to an event, such as when baseline generator input data is being generated at block 212 of routine 200, when an individual item of health care data is to be processed by a baseline generator at block 214 of routine 200, etc. When routine 400 is initiated, a set of executable program instructions stored on one or more non-transitory computer-readable media (e.g., hard drive, flash memory, removable media, etc.) may be loaded into memory (e.g., random access memory or "RAM") of a computing device. In some embodiments, routine 400 may be part of routine 200 (e.g., part of blocks 212 and 214), even though routine 400 is illustrated and described separately from routine 200. In some embodiments, routine 400 or portions thereof may be implemented on multiple processors (on the same or separate computing devices), serially or in parallel.

At block 404, the health care processing system 100 may determine an identifying characteristic of a health care data item to be processed. The identifying characteristic may be an identifier, such as a code, for a claim or individual line item of a claim. For example, if a claim includes a line item for a procedure, good, or service, the health care processing system 100 may identify a code for the procedure, good, or service.

At decision block 406, the health care processing system 100 may determine that the health care data item includes non-standard health care data. In some embodiments, the health care processing system 100 may determine that a particular record or portion of the health care data item includes a code that is not recognized by, or otherwise unable to be processed by, the selected baseline generator 112. For example, a health care entity may use a particular code for a line item, representing a procedure, good, or service, as identified above. The selected baseline generator 112 may not recognize the code, or may require more fine-grained detail about the service (e.g., individual steps that were performed to provide the service, individual goods that were consumed, etc.). If the health care processing system 100 determines that the health care data item does not include any non-standard health care data, the routine 400 may proceed to block 408. Otherwise, if the health care data item includes non-standard health care data, the routine 400 may proceed to block 410.

At block 408, the baseline generator 112 may process the current health care data item. As described above, processing the health care data item may include generating one or more output records corresponding to each input record, such as output records for the input line item. Illustratively, the output records may include information about the input line item, such as eligibility, valuation, etc. The routine 400 may then end at block 418.

At block 410, after the health care processing system 100 has determined that the current health care data item includes non-standard health care data, the health care processing system 100 can determine substitute or replacement health care data that provides sufficient information for—or is otherwise in format able to be processed by—the baseline generator 112. In some embodiments, the health care processing system 100 may determine to replace a line item with another line item (e.g., 1-to-1) so that a recognized code is present for the baseline generator 112. In some embodiments, the health care processing system 100 may determine to replace a line item by expanding it into multiple line items (e.g., 1-to-many). For example, if a single line item refers to a procedure that the baseline generator 112 is not configured to process and for which there is no 1-to-1 replacement, then the health care processing system 100 can use one or more conversion rules to expand the line item. Illustratively, a conversion rule may be associated with the identifying code for the line item and/or the baseline generator 112. The conversion rule may specify that the health care data item associated with the particular identifying code is to be converted into, or replaced by, multiple health care data items that are considered to collectively represent the procedure, good, or service of the line item.

At block 412, the health care processing system 100 generate substitute or replacement health care data. For example, the health care processing system 100 can use a conversion rule as determined above. In some embodiments, when the health care processing system 100 applies a conversion rule, the application may involve executing a subroutine that handles the conversion, accessing a table that includes the data to be used in place of the non-standard data, another operation, some combination thereof, etc.

At block 414, the health care processing system can process the substitute health care data generated above. As described above, processing the health care data item may include generating one or more output records corresponding to each input record, such as output records for the input line item. Illustratively, the output records may include information about the input line item, such as eligibility, valuation, etc.

At block 416, the health care processing system 100 can convert the processed substitute health care data to the format of the original health care data item, or to a format compatible with the format of the original health care data item. The health care processing system 100 may use one or more conversion rules which may be the same as, inverses of, or independent from, the conversion rules used to convert the health care data item to the substitute health care data. For example, the original health care data item was converted to substitute health care data in a 1-to-1 conversion by replacing an identifying code. In this case, converting the processed substitute health care data may include changing the code of the substitute health care data back to the original identifying code. As another example, the original health care data item was converted to substitute health care data in a 1-to-many conversion by expanding the procedure, good, or service into multiple line items. In this case, converting the processed substitute health care data may include aggregating the separate substitute line items (e.g., by summing the determined valuations) into a single line item. At block 418, the routine may end.

FIG. 5 is a flow diagram of an example routine 500 executed by the health care processing system 100 to determine an algorithm for use in processing baseline data. The example routine 500 includes the selection of a claim processor 114, or the parameters for an augmentation algorithm embodied by or executed by a claim processor 114, based on one or more criteria associated with a health care claim.

Routine 500 begins at block 502. Routine 500 may begin in response to an event, such as when baseline data has been generated and is ready to be processed at block 220 of routine 200. When routine 500 is initiated, a set of executable program instructions stored on one or more non-transitory computer-readable media (e.g., hard drive, flash memory, removable media, etc.) may be loaded into memory (e.g., random access memory or "RAM") of a computing device. In some embodiments, routine 500 may be part of routine 200 (e.g., part of block 220), even though routine 500 is illustrated and described separately from routine 200. In some embodiments, routine 500 or portions thereof may be implemented on multiple processors (on the same or separate computing devices), serially or in parallel.

At block 504, the health care processing system 100 may determine one or more properties associated with the consumer of health care services that are the subject of the claim to be processed. In some embodiments, the properties may include identifying information for individuals and/or groups. For example, the claim may be associated with a particular group of consumers (e.g., a group of individuals who collectively obtain health care coverage, such as a particular company that provides coverage to employees). As another example, the claim may be associated with a particular consumer, such as a particular patient. The baseline data representing the claim may include an identifier for the consumer and/or group.

At block 506, the health care processing system 100 may determine one or more properties associated with the provider of the health care services that are the subject of the claim to be processed. In some embodiments, the properties may include identifying information for the individual provider of the health care services (e.g., the physician), the facility at which the services were proved (e.g., the hospital), etc. The baseline data representing the claim may include an identifier for the provider and/or facility.

At block 508, the health care processing system 100 may determine one or more properties of the claim to be processed. In some embodiments, the properties may include the date(s) of service (e.g., start date and/or end date of the health care services that are the subject of the claim to be processed), the type of services provided (e.g., inpatient, outpatient, hospice, etc.), a health care service group (e.g., a classification that represents a set of multiple related services and/or goods that are provided in connection with the claim to be processed), etc. The baseline data representing the claim may include data, identifiers for the type of services and/or health care service group, etc.

At block 510, the health care processing system 100 can determine the claim processors(s) 114 (or the augmentation algorithm(s) to be used by the claim processor(s) 114) that are applicable for the current claim, based some or all of the information determined above. Illustratively, the health care processing system 100 can determine which claim processor(s) 114, active for the date(s) of service for the claim being processed, is/are also associated with one or more of: the individual consumer, the group of consumers, the provider, the facility, the type of services, the health care service group, other properties, or some combination thereof. A claim processor 114 may be associated with a group or individual consumer if it is assigned to, limited to use with, or otherwise linked to the group or consumer of the health care services that are the subject of the claim to which the claim belongs. A claim processor 114 may be associated with a type of service or health care service group if the augmentation algorithm is assigned to, limited to use with, or otherwise linked to the type of service or health care service group.

In some embodiments, a claim processor 114 may be configured to execute an augmentation algorithm that includes steps of: determining a type of service associated with the claim; determining a rate by which the baseline valuation for the type of service is to be adjusted; and applying the rate to determine the final amount. For example, if a claim for a consumer in a particular group of consumers is an outpatient claim, the baseline valuation may be adjusted by a first factor (e.g., a percentage), while if the claim is an inpatient claim the baseline valuation may be adjusted by a second factor (e.g., a different percentage).

In some embodiments, a claim processor 114 may be configured to execute an augmentation algorithm that includes steps of: determining a health care service group associated with the claim; determining a flat fee for the health care service group; and setting the final valuation to the value of the flat fee. For example, if a claim for a consumer in a particular group of consumers, or a particular provider or facility, is a claim associated with a particular health care service group (e.g., the claim is for treating a broken arm), the flat rate may be substituted for the baseline valuation, if any.

In some embodiments, a claim processor 114 may be configured to execute an augmentation algorithm that includes steps of: determining a health care service group associated with the claim; determining a factor associated with a particular health care entity (e.g., consumer or provider), and using the factor to adjust the baseline valuation (or a flat fee associated with the health care service group) to determine the final valuation of the claim. For example, if a claim for a consumer in a particular group of consumers, or a particular provider or facility, is a claim associated with a particular health care service group (e.g., the claim is for treating a broken arm), the flat rate or baseline valuation determined for the health care service group may be adjusted using the determined factor.

In some embodiments, a claim processor 114 may be configured to execute an augmentation algorithm that includes steps of: determining a factor associated with a particular property or combination of properties of the claim (e.g., consumer, provider, type of service); and using the factor to adjust the baseline amount to determine the final valuation of the claim. For example, if a claim for a consumer in a particular group of consumers is associated with a particular type of service, then an associated factor may be applied to the baseline valuation to determine the valuation.

In some embodiments, a claim processor 114 may be configured to execute an augmentation algorithm that includes steps of: determining a factor associated with a particular property or combination of properties of the claim (e.g., consumer, provider, type of service); and using the factor to adjust the original charged amount of the claim (as opposed to the baseline valuation) to determine the final valuation of the claim. For example, if a claim for a consumer in a particular group of consumers is associated with a particular type of service, then an associated factor may be applied to the original charged amount for the claim.

In some embodiments, a claim processor 114 may be configured to execute an augmentation algorithm that includes steps of: determining a global or default factor; and using the factor to adjust either the original charged amount of the claim or the baseline amount of the claim to determine the final valuation of the claim. For example, if a claim is not associated with any other more specific claim processor 114, such as those described above, then the global or default factor may be applied to the original charged amount or the baseline amount to determine the final amount for the claim.

In some embodiments, a claim processor 114 may be configured to execute multiple augmentation algorithms, and select a particular algorithm—or the output of a particular algorithm—based on one or more rules or criteria. For example, if multiple algorithms are applicable for a particular claim as discussed in greater detail below, a claim processor 114 may execute each augmentation algorithm, and then average the results, take the minimum or maximum of the results, etc.

At decision block 512, the health care processing system 100 can determine whether there are multiple claim processors 114 (or augmentation algorithms) identified above. If so, the routine 500 can proceed to block 514. Otherwise, the process 500 can proceed to block 516.

At block 514, the health care processing system 100 can determine the priority of the multiple claim processors 114 determined above. The health care processing system 100 can then use the highest priority claim processor 114 to process the claim. In some embodiments, the priority may be determined using a hierarchy based on the particular properties of the claims with which the individual claim processors 114 are associated. For example, claim processors 114 associated with the individual consumer may take the highest priority. Claim processors 114 associated with the particular facility may take the next highest priority. Claim processors 114 associated with the consumer group may take the next highest priority. Finally, global or default claim processors 114 may be used if no claim processors 114 at a higher level of the hierarchy applicable to the current claim. The example priority hierarchy is illustrative only, and not intended to be limiting. In some embodiments, a hierarchy may have fewer, additional, and/or alternative levels, the levels may be in a different order, etc. In some embodiments, individual claim processors 114 may be associated with absolute or relative priority assignments that are used instead of, or in addition to, properties of the claims with which individual claim processors 14 are associated.

At block 516, the health care processing system 100 can determine a final valuation for the claim using the selected claim processor 114. The routine 500 may end at block 518.

Interactive Health Care Data User Interfaces

Figure 6:
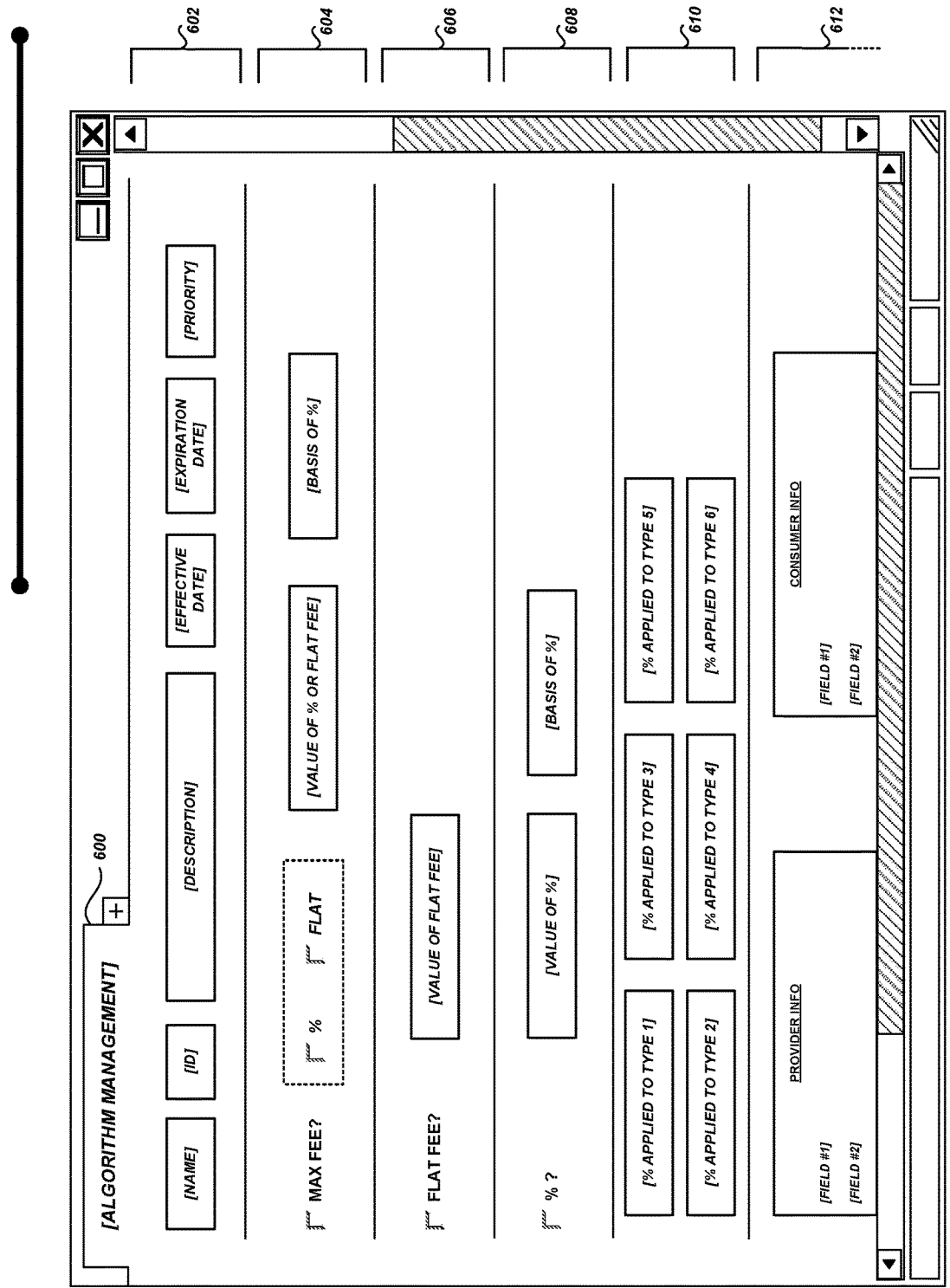
FIG. 6 is a user interface diagram for managing an augmentation algorithm according to some embodiments.

FIG. 6 is a user interface diagram of an illustrative user interface 600 for creating and maintaining parameters for a claim processor 114. The user interface 600—also referred to as an augmentation algorithm management interface 600—includes various sections for providing and/or modifying information used to manage the claim processor 114 or during execution of the augmentation algorithms of the claim processor 114. For example, a general information section 602 may provide controls for entry of name information, identifying information, description information, and the like. Some controls may provide management of particular operational parameters for selecting and using the claim processors 114. For example, the general information section 602 may also include controls for effective and/or expiration date information, priority information, and the like. The effective/expiration date information may be used to determine whether the claim processor 114 is applicable to a claim being processed, while the priority information may be used to determine whether the claim processor 114 takes priority over other claim processors 114 if there are multiple claim processors 114 applicable to a particular claim.

Augmentation algorithm management interface 600 may include a maximum valuation section 604 for providing and maintaining maximum valuation information. In some embodiments, the maximum valuation section 604 may include controls to indicate whether a maximum valuation is to be used, whether the maximum valuation is a percentage or flat fee, the particular amount to which the percentage applies, and the like. The maximum valuation information may be used by the claim processor 114 to determine whether the valuation for a claim, as determined by a baseline generator 112 and/or adjusted by other operations of the claim processor 114, exceeds a maximum amount that may be determined for the claim. The maximum amount may be a flat fee (e.g., an upper limit). Alternatively, the maximum amount may be dynamically computed as a percentage of another amount, such as a baseline valuation (e.g., 200% of baseline valuation) or the initial amount of the claim.

Augmentation algorithm management interface 600 may include a flat fee section 606 for providing and maintaining flat fee information. In some embodiments, the claim processor 114 may be configured to apply a flat fee to the claims, regardless of what valuation is determined by the baseline generator 112. The amount specified in the flat fee section 606 may be used in these cases.

Augmentation algorithm management interface 600 may include a valuation factor section 608 for providing and maintaining valuation factor information. In some embodiments, the claim processor 114 may be configured to apply a factor to a previously-determined amount, such as the amount determined by the baseline generator 112 or the original claim amount. In such cases, the factor specified in the valuation factor section 608 may be applied to the particular base amount specified in the valuation factor section 608.

Augmentation algorithm management interface 600 may include a detail section 610 for providing and maintaining detailed valuation and factor information for different types and components of a claim. In some embodiments, the claim processor 114 may be configured to apply different factors to different types of valuations, such as different line items of a claim. When the claim processor 114 is processing a claim and encounters a line item, the claim processor may determine the type of service or good to which the line items applies. The claim processor 114 may then determine the corresponding factor, as specified in the detail section 610, to be applied to the amount of the line item in the input data for the claim processor 114. For example, the claim processor 114 may apply the same or different factors to inpatient fees, outpatient fees, critical access fees, pediatric fees, ambulatory fees, hospice fees, psychiatric fees, skilled nursing fees, home health care fees, rehabilitation fees, hospitalization fees, overall baseline generator determined fees, individual schedule item fees, other fees, some combination thereof, etc.

Algorithm management interface 600 may include a related entities section 612 for associating the claim processor 114 with one or more health care entities. In some embodiments, the claim processor 114 may applied to a selected entity or group of entities, such as a provider of health care services (e.g., a physician or facility), a consumer of health care services (e.g., an individual or group of individual), other entities, groups thereof, combinations thereof, etc. The particular entities may be specified and maintained in the related entities section 612.

Figure 7:
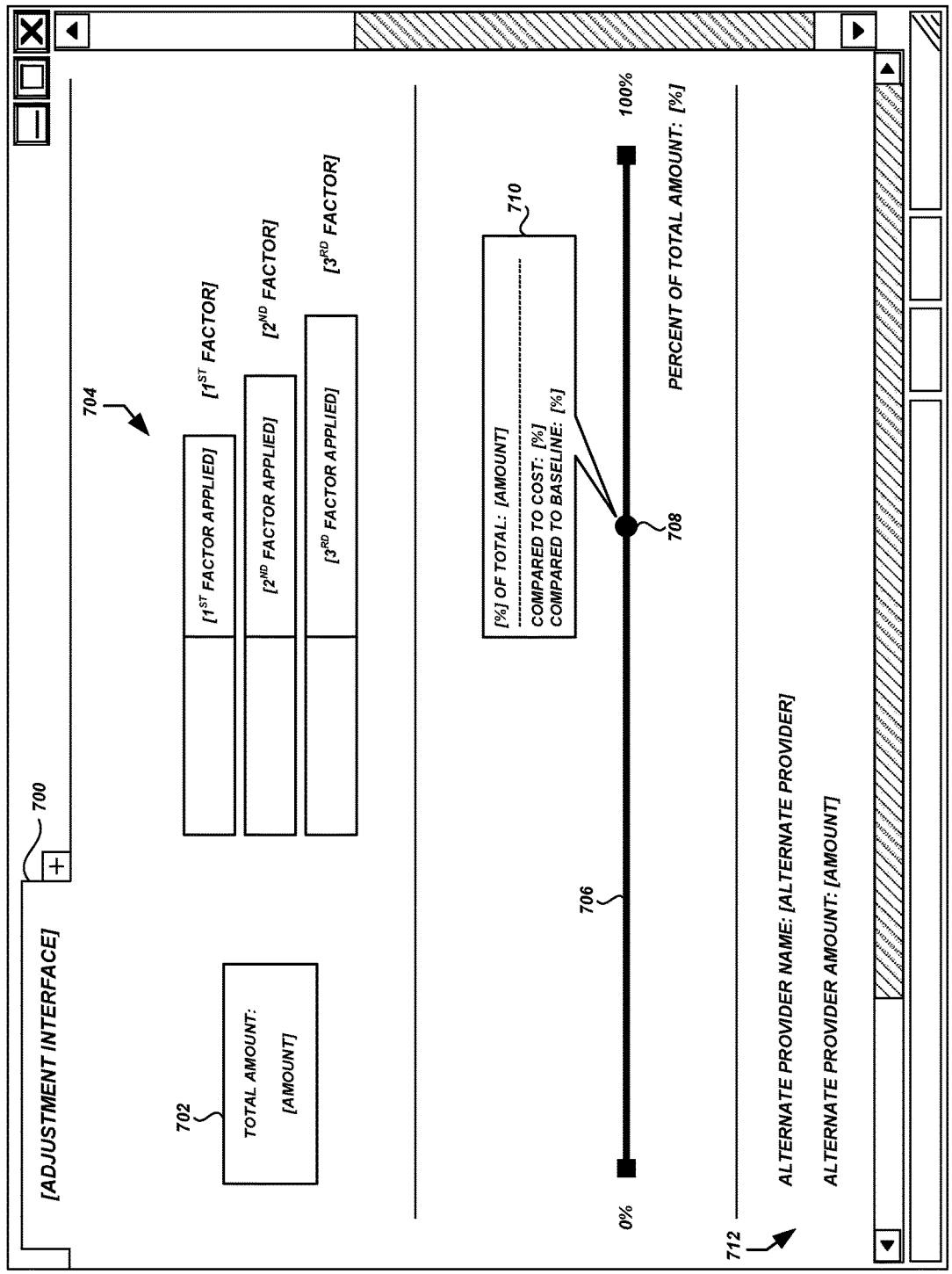
FIG. 7 is a user interface diagram showing a dynamic adjustment control for health care data according to some embodiments.

FIG. 7 is a user interface diagram of an illustrative user interface 700 for applying an adjustment to a health care record, such as modifying claim information. In some embodiments, as shown, the user interface 700—also referred to as an adjustment interface 700—may include a claim overview section 702 to present information about a particular claim, such as the amount generated by the baseline generator 112, the original amount of the claim (e.g., in the health care data file), the costs incurred by the provider associated with the claim (e.g., determined using a database of provider costs, rather than from the health care data file), other information, some combination thereof, etc. The adjustment interface 700 may include an adjustment overview section 704 to present information about how different adjustments to the claim will affect the total of the claim. For example, the adjustment overview section 704 may present the result of applying various factors to an amount shown in the claim overview section 702 (e.g., presenting 150%, 175%, and 200% of the baseline generator 112 determined amount, the costs incurred by the provider, etc.).

The adjustment interface 700 may be interactive and dynamic to allow for real-time adjustments to the claim information. The adjustment interface 700 may include an interactive adjustment control 706 to adjust the factor applied to an amount associated with the claim. For example, the interactive adjustment control 706 may be a dynamic slider with a movable point 708. A user may move the point 708 between two adjustment limits, such as an upper limit and a lower limit. The limits may correspond to the upper and lower limits for a factor to be applied to the claim information. In one specific, non-limiting embodiment, a user may move the point 708 between a lower limit of 0% and an upper limit of 200%. The specific location of the point 708 on the adjustment control 706 at any given time may be converted to a factor between the upper and lower limits based on the distance of the point 708 from the upper and/or lower limits. The factor may be applied to the claim information at issue, such as the amount determined by the baseline generator 112.

A real-time adjustment detail section 710 may present information that changes in real-time as the user interacts with the adjustment control 706. For example, the real-time adjustment detail section 710 may present the current factor that is applied to the claim information, the result of applying the current factor to the claim information, a comparison of the adjusted claim information to other claim information (e.g., a comparison of the adjusted original amount to the output of the baseline generator 112 and/or the costs incurred by the provider), etc.

The adjustment interface 700 may include an alternate provider section 712 to display information regarding one or more alternate providers. In some embodiments, the alternate providers may be selected from within a particular geographic region (e.g., the same city or state as the provider associated with the current claim), or within a threshold distance of the current provider (e.g., within 10 miles, 25 miles, 50 miles, etc.). The alternate provider section 712 may be used to indicate that one or more providers are predicted to provide the same or substantially the same services as are the subject of the current claim for the lowest overall valuation.

The adjustment interface 700 may be useful when determining how to handle claims that have disputed aspects. In some embodiments, a claim may be determined to have a disputed aspect if the provider has rejected the final valuation determined by the health care processing system 100. A user may then use the adjustment interface 700 to quickly and easily see a comparison of different relevant information, and to test adjustments to the claim information and obtain the results in real time. Thus, the adjustment interface 700 can provide results to a user more quickly and comprehensively than requiring the user to input amounts into a calculator, compute adjustments, view results, try different adjustments, etc.

Figure 8:
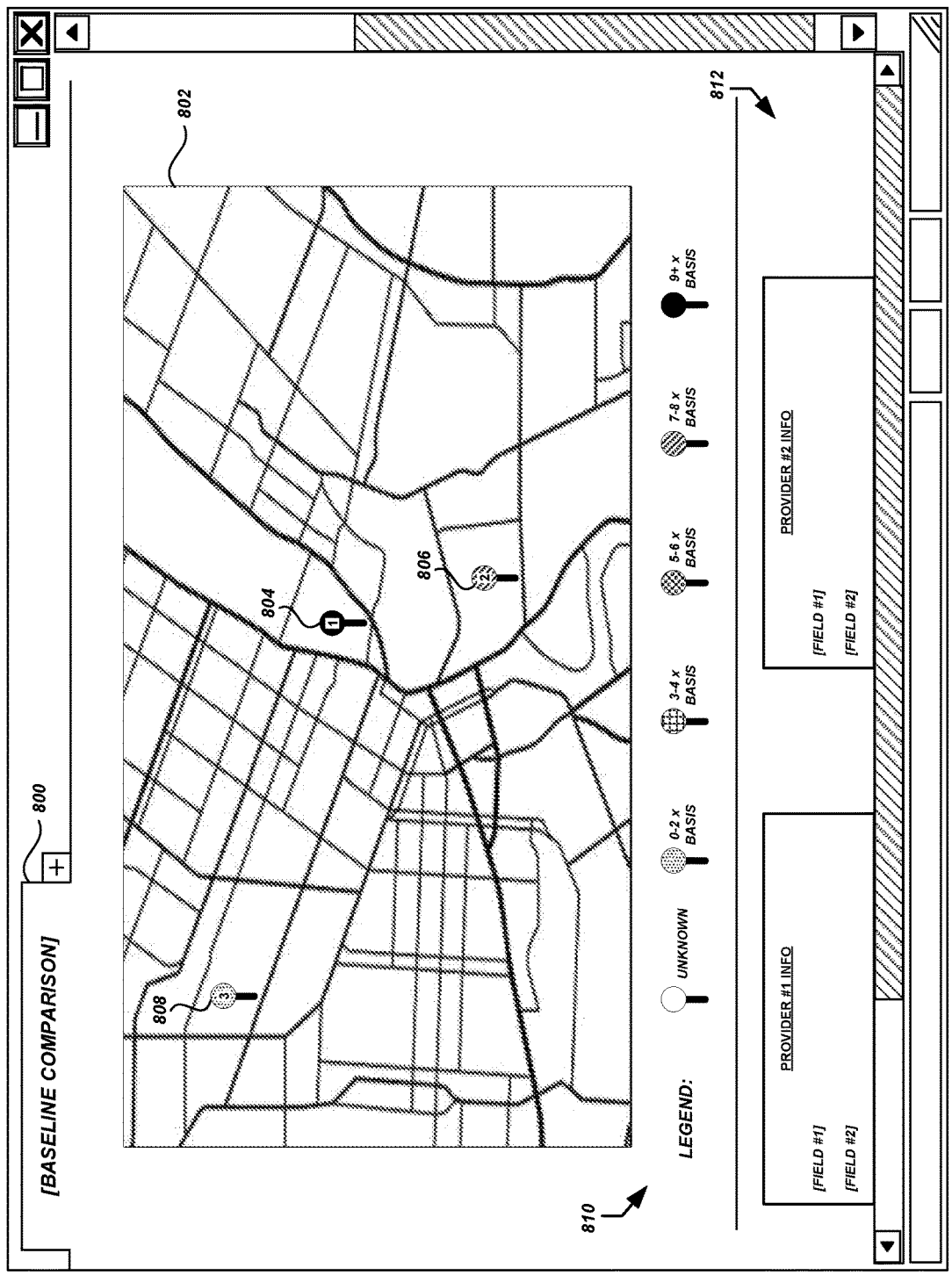
FIG. 8 is a user interface diagram showing health care service providers in a geographic area and corresponding provider-specific data for comparison according to some embodiments.

FIG. 8 is a user interface diagram of an illustrative user interface 800 for presenting information regarding providers within a geographic region, or within a threshold distance of a geographic location. The presentation of information may be based on the degree to which individual providers charge or otherwise have claims with amounts that exceed a basis, such as baseline generator output, costs incurred by the providers to provide the services that are the subject of claims, etc. For example, the amount claimed by a provider for a particular service may be compared to the baseline generator output amount for the service, and a ratio, multiple, or other factor may be generated. The factor for the provider may be used to compare the provider to other providers when factors for the other providers are generated. Thus, the user interface 800—also referred to as a baseline comparison interface 800—may be used to quickly and visually compare providers against each user, using the same metric, across a geographic region.

The baseline comparison interface 800 may include a map 802 on which objects representing individual providers may be displayed. As shown, a first provider may be represented by a first object 804. Additional providers that are in the same geographic region as the first provider (e.g., same city or state), or within a threshold geographic distance of the first provider (e.g., 10 miles, 25 miles, 50 miles, etc.) may also be shown on the map. For example, a second provider may be represented by a second object 806, a third provider may be represented by a third object 808, etc.

The objects 804, 806 that represent individual providers may have visual aspects indicative of the degree to which their respective valuations compare to the baseline being used. For example, the factor itself may be displayed on or in connection with the objects 804, 806. As another example, the color, texture, and/or size of the objects 804, 806 may be used to indicate the factor. In some embodiments, a legend 810 may be presented or accessible to the user. The legend 810 may provide the factor represented by the various visual characteristics of the objects 804-808.

Additional detail information may be presented about the individual providers 804-808. For example, a detail section 812 may include identifying information regarding the providers, quality information (e.g., ratings, reviews, etc.), information about the data underlying the factors determined for the individual providers, etc. In some embodiments, users may be able to select individual providers—either in the map 802 or the detail section 812—and be presented with an interface for more detailed information and interaction options associated with the particular provider.

Figure 9:
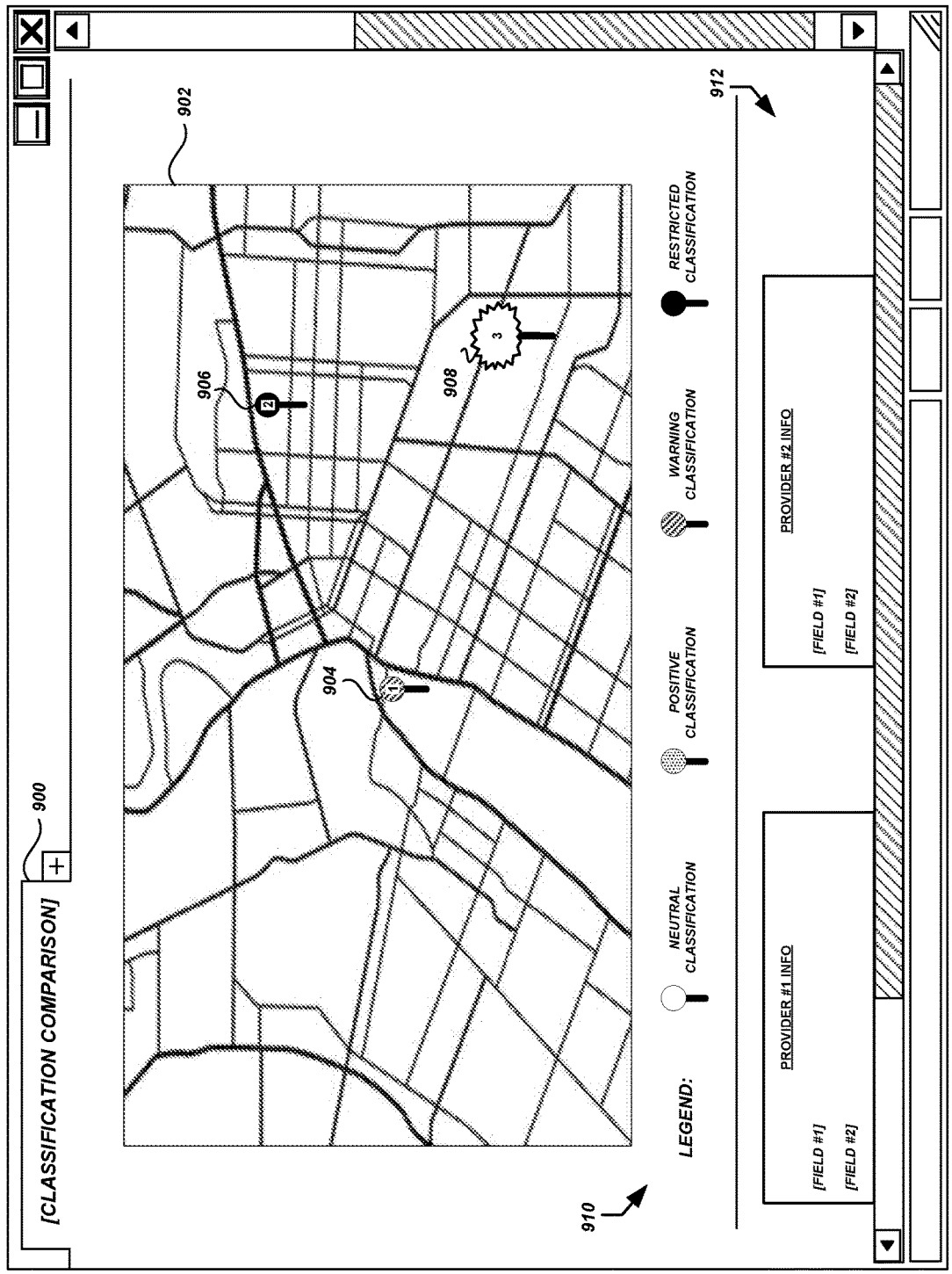
FIG. 9 is another user interface diagram showing health care service providers in a geographic area and corresponding provider-specific data for comparison according to some embodiments.

FIG. 9 is a user interface diagram of an illustrative user interface 900 for presenting information regarding providers within a geographic region, or within a threshold distance of a geographic location. The presentation of information may be based on a classification to which individual providers have been assigned based on the experience of the health care processing system 100 dealing with claims of the provider. The classification may represent the estimated likelihood that a provider will accept the valuation determined by the health care processing system 100, or otherwise that there will not be a dispute of the valuation determined by the health care processing system 100.

Figure 10:
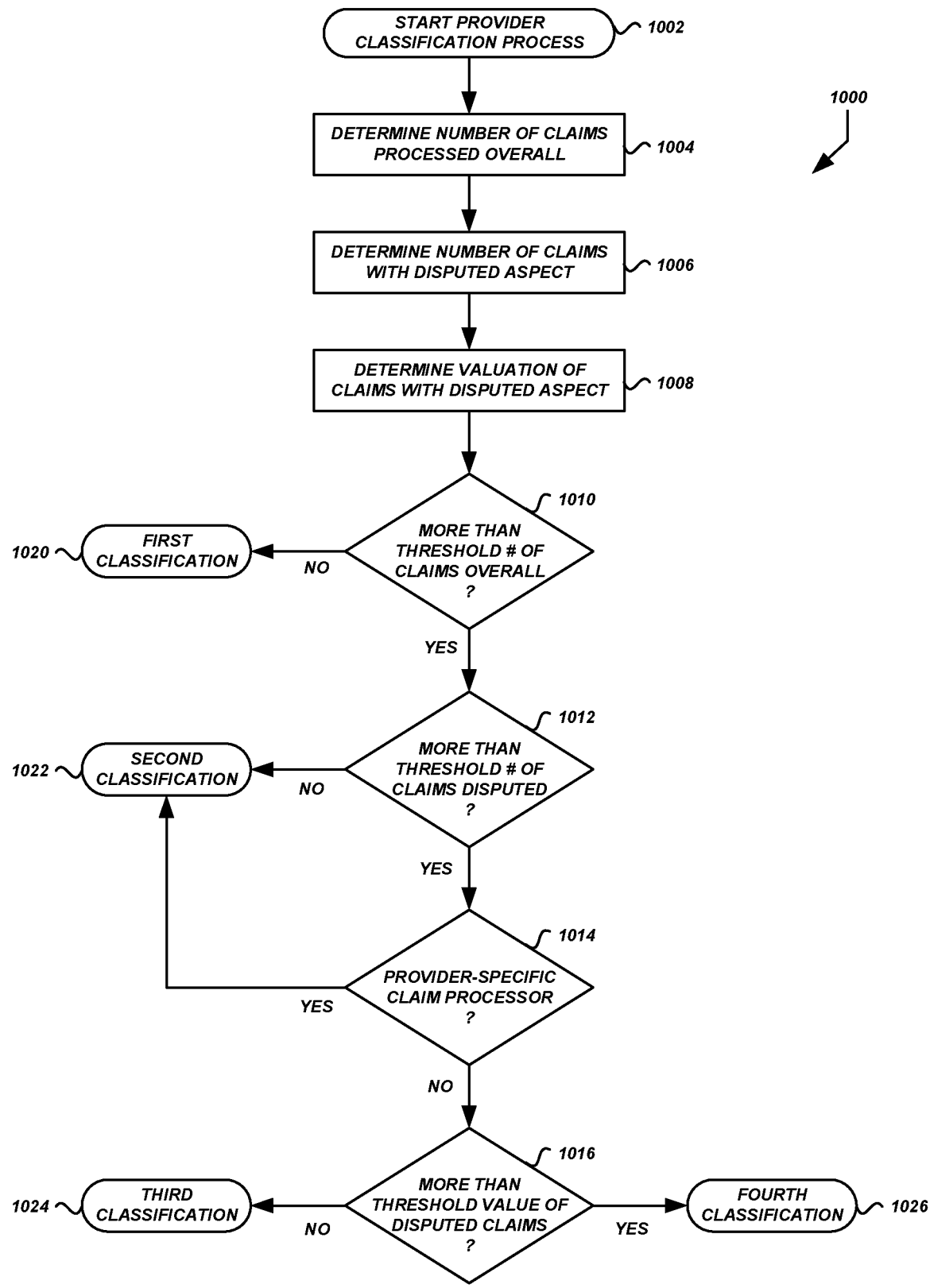
FIG. 10 is a flow diagram of an illustrative routine for determining health care service provider classifications according to some embodiments.

For example, individual providers may be assigned to classifications based on historical data associated with the providers. An example routine for determining classifications is shown in FIG. 10 and described in greater detail below. The classification for a provider may be used to compare the provider to other providers. Thus, the user interface 900—also referred to as a classification comparison interface 900—may be used to quickly and visually compare providers against each user, using the same set of classifications, across a geographic region.

The classification comparison interface 900 may include a map 902 on which objects representing individual providers may be displayed. As shown, a first provider may be represented by a first object 904. Additional providers that are in the same geographic region as the first provider (e.g., same city or state), or within a threshold geographic distance of the first provider (e.g., 10 miles, 25 miles, 50 miles, etc.) may also be shown on the map. For example, a second provider may be represented by a second object 906, a third provider may be represented by a third object 908, etc.

The objects 904-908 that represent individual providers may have visual aspects indicative of the classification to which the respective providers have been assigned. For example, a label of the classification may be displayed on or in connection with the objects 904-908. As another example, the color, texture, and/or size of the objects 904-908 may be used to indicate the classification. In some embodiments, a legend 910 may be presented or accessible to the user. The legend 910 may provide the classification represented by the various visual characteristics of the objects 904-908. In some embodiments, different display objects or certain visual characteristics may be used to convey additional information about a provider. For example, a provider that has a provider-specific claim processor 114 or is otherwise a "preferred" provider may be indicated as such using a different display object such as the star shown in object 908. In this way, users may get an indication of which providers are preferred providers for a prospective health care service.

The providers may be assigned to classifications representing the likelihood that they will accept valuations overall as determined by the health care processing system. In some embodiments, the providers may be assigned to classifications on a more granular level. For example, the classification may represent the likelihood that a provider will accept valuations for a particular service type, a particular DRG, or a particular line item. Thus, a single provider may be associated with multiple classifications.

The classification comparison interface 900 may be useful when determining which provider to use for obtaining a particular service. By presenting a visual comparison of providers in a given geographic area, showing the respective likelihoods that the providers are expected to accept valuations determined by the health care processing system 100, a user can quickly and easily choose the provider that is least likely lead to a dispute. Additional information about individual providers may also be presented, such as a rating of quality, a rating of customer experience, an indication that the provider has a specific claim processor 114 available for the desired service, etc.

Additional detail information may be presented about the individual providers 904-908. For example, a detail section 912 may include identifying information regarding the providers, quality information (e.g., ratings, reviews, etc.), information about the data underlying the classifications determined for the individual providers, etc. In some embodiments, users may be able to select individual providers—either in the map 902 or the detail section 912—and be presented with an interface for more detailed information and interaction options associated with the particular provider.

FIG. 10 is a flow diagram of an example routine 1000 executed by the health care processing system 100 to determine an acceptance classification for a provider of health care services. The acceptance classification may be used by the health care processing system 100 in a variety of ways, such as to determine which providers to recommend to a user, to determine presentation characteristics that convey the acceptance rating to users, etc.

Routine 1000 begins at block 1002. Routine 1000 may begin on a predetermined or dynamically determined schedule, or in response to an event such as when the user interface server 116 is generating a user interface that will include presentation of provider-specific information. When routine 1000 is initiated, a set of executable program instructions stored on one or more non-transitory computer-readable media (e.g., hard drive, flash memory, removable media, etc.) may be loaded into memory (e.g., random access memory or "RAM") of a computing device. In some embodiments, routine 1000 or portions thereof may be implemented on multiple processors (on the same or separate computing devices), serially or in parallel.

At block 1004, the health care processing system 100 may determine, for a particular provider, the number of claims that have been processed by the health care processing system 100.

At block 1006, the health care processing system 100 may determine, for the current provider, the number of claims with a disputed aspect that have been processed by the health care processing system 100. In some embodiments, a claim may be determined to have a disputed aspect if the provider has rejected or objected to the final valuation determined by the health care processing system 100.

At block 1008, the health care processing system 100 may determine, for the current provider, a cost of each of the claims with a disputed aspect that have been processed by the health care processing system 100.

At decision block 1010, the health care processing system 100 can determine whether it has processed more than a threshold number of claims associated with the current provider. For example, the health care processing system 100 may be configured to use a first threshold value (e.g., 10). If the number of claims processed by the health care processing system 100 for the current provider fails to satisfy the first threshold (e.g., the number is below the first threshold), then the provider may be assigned to a first classification 1020. Illustratively, the first classification may be a neutral or baseline classification indicating that there is not enough history with the provider to make a well-supported classification decision. If the number of claims processed by the health care processing system 100 for the current provider satisfies the first threshold (e.g., the number meets or exceeds the first threshold), then the routine 1000 may proceed to decision block 1012.

At decision block 1012, the health care processing system 100 can determine whether it has processed more than a threshold percentage of claims, associated with the current provider, that have a disputed aspect. For example, the health care processing system 100 may be configured to use a second threshold value (e.g., 10%). If the percentage of claims with a disputed aspect for the current provider fails to satisfy the second threshold (e.g., the percentage is below second threshold), then the provider may be assigned to a second classification 1022. Illustratively, the second classification may be a positive or approved classification indicating that there is enough history with the provider—and the history is positive enough—to determine that the provider is preferred or approved. If the percentage of claims with a disputed aspect for the current provider satisfies the second threshold (e.g., the percentage meets or exceeds the second threshold), then the routine 1000 may proceed to decision block 1014.

At decision block 1014, the health care processing system 100 can determine whether there is a provider-specific claim processor 114 for the provider. For example, after a threshold number or percentage of claims with disputed aspects for the provider have been identified, the health care processing system 100 may be configured with a provider-specific claim processor 114 to process future claims in a manner that reduces or eliminates disputes. If there is provider-specific claim processor 114 for the current provider, then the provider may be assigned to the second classification 1022. Otherwise, the routine 1000 may proceed to decision block 1016.

At decision block 1016, the health care processing system 100 can determine whether a threshold number or percentage of claims with a disputed aspect for the current provider have been settled at greater than a threshold amount. For example, the health care processing system 100 may use a fourth threshold percentage of baseline generator determined valuation for the claim (e.g., 200% of baseline percentage) to determine whether a claim has been settled unfavorably or otherwise unsatisfactorily. If the amount of such claims for the current provider fails to satisfy a fifth threshold amount or percentage (e.g., 40%), then the provider may be assigned to a third classification 1024. Illustratively, the third classification 1024 may be a warning classification. Otherwise, if the amount of such claims for the current provider satisfies the fifth threshold amount or percentage, then the provider may be assigned to a fourth classification 1026. Illustratively, the fourth classification may be a restricted classification. In some embodiments, obtaining services from providers assigned to the fourth classification may require pre-approval.

The example provider classifications described herein are illustrative only, and not intended to be limiting. In some embodiments, the routine 1000 may determine fewer, additional, and/or alternative classifications, the classifications may be in a different order, etc.

Example Device Components

FIG. 11 is block diagram of various components of a computing device configured to provider features of the present disclosure according to some embodiments. FIG. 11 shows components of an illustrative health care service provider 100 computing device 1100. In some embodiments, as shown, the computing device 1100 may include: one or more computer processors 1102, such as physical central processing units ("CPUs"); one or more network interfaces 1104, such as a network interface cards ("NICs"); one or more computer readable medium drives 1106, such as a high density disk ("HDDs"), solid state drives ("SDDs"), flash drives, and/or other persistent non-transitory computer-readable media; and one or more computer readable memories 1108, such as random access memory ("RAM") and/or other volatile non-transitory computer-readable media. The computer readable memory 1108 may include computer program instructions that the computer processor 1102 executes in order to implement one or more embodiments. For example, the computer readable memory 1108 can store an operating system 1110 that provides computer program instructions for use by the computer processor 1102 in the general administration and operation of the computing system 1100. The computer readable memory 1108 may also include file processor instructions 1112 for performing the functions of the file processor 110. The computer readable memory 1110 may also include baseline generator instructions 1114 for performing the functions of the baseline generator(s) 112. The computer readable memory 1110 may also include claim processor instructions 1116 for performing the functions of the claim processor(s) 114. The computer readable memory 1110 may also include user interface server instructions 1118 for performing the functions of the user interface server 116.

Terminology

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware, or combinations of electronic hardware and computer software. To clearly illustrate this interchangeability, various illustrative components, blocks, modules, and steps have been described above generally in terms of their functionality. Whether such functionality is implemented as hardware, or as software that runs on hardware, depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a computing processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A computer processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

What is claimed is:

1. A system comprising computer-readable memory and one or more computer processors, wherein the system is configured to at least:

receive one or more health care data records associated with a health care claim of a health care service provider;

determine a health care baseline algorithm of a plurality of health care baseline algorithms based at least partly on an attribute of the health care claim;

determine that a first health care data record comprises a non-standard code representing a health care service not included in a list of coded health care services associated with the health care baseline algorithm;

determine a plurality of standard codes to collectively replace the non-standard code;

update the first health care data record by replacing the non-standard code with the determined plurality of standard codes;

generate baseline data, representing a baseline amount for a health care service associated with the health care claim, using the one or more health care data records and the health care baseline algorithm;

generate first display instructions for a health care data adjustment interface comprising:

a health care data overview portion that presents the baseline amount;

a real-time adjustment detail portion that presents a result of adjusting health care data regarding the health care service in substantially real-time; and an interactive adjustment control, wherein a user interaction with the interactive adjustment control occurring after display of the health care data adjustment interface causes a change to an adjustment factor applied to the health care data, and wherein the real-time adjustment detail portion automatically updates, in response to the user interaction with the interactive adjustment control, presentation of:

a first result of adjusting the health care data using the changed adjustment factor; and a second result of analyzing the baseline amount with respect to the first result; and generate second display instructions for a health care service provider comparison interface comprising:

a map of a geographic area in which a first health care service provider is located;

a first object representing a location of the first health care service provider within the geographic area, wherein a visual property of the first object represents a classification, of a plurality of predetermined claim valuation acceptance classifications, to which the first health care service provider is assigned based on historical experience processing health care data records associated with the first health care service provider, and wherein the historical experience processing health care data records is based on (1) a degree to which the first health care service provider accepts health care claim processing based at least in part on a plurality of health care baseline amounts, and (2) acceptance status of the health care data associated with the health care data adjustment interface; and a second object representing a location of a second health care service provider within the geographic area, wherein a visual property of the second object represents a classification to which the second health care service provider is assigned based on historical experience processing health care data records associated with the second health care service provider.

2. The system of claim 1, wherein the interactive adjustment control comprises a slider control, wherein a user interaction with the slider control causes a portion of the slider control to move toward a first limit and away from a second limit, and wherein a value of the adjustment factor is based on a relative position of the portion of the slider control with respect to at least one of the first limit or the second limit.

3. The system of claim 1, wherein the real-time adjustment detail portion further presents information regarding at least one of: a current value of the adjustment factor, a comparison of adjusted health care data to the baseline amount, or a comparison of adjusted health care data to costs incurred by the first health care service provider to provide the health care service.

4. The system of claim 1, further configured to at least determine that the second health care service provider is likely to generate a health care claim including a value that is less than a value in a health care claim generated by the first health care service provider for the health care service, wherein the health care data adjustment interface further comprises an alternate provider section that presents information regarding the second health care service provider.

5. The system of claim 1, wherein the visual property of the first object comprises one of: a color of the first object, a texture of the first object, or a label assigned to the first object.

6. The system of claim 1, wherein the historical experience processing health care data records associated with the first health care service provider comprises experience processing disputed health care claims associated with the first health care service provider.

7. The system of claim 1, wherein the historical experience processing health care data records associated with the first health care service provider comprises experience comparing health care claims associated with the first health care service provider to at least one of: a baseline amount, or an amount of expenses incurred by the first health care service provider.

8. The system of claim 1, further configured to determine the classification to which the first health care service provider is assigned based at least partly on an analysis of health care data records regarding a particular health care service provided by the first health care service provider.

9. The system of claim 1, further configured to determine the classification based at least partly on a predicted likelihood of the first health care service provider disputing a health care claim associated with a particular health care service.

10. A computer-implemented method comprising:

as implemented by a computing system comprising one or more computer processors configured to execute specific instructions:

receiving one or more health care data records associated with a health care claim of a health care service provider;

determining a health care baseline algorithm of a plurality of health care baseline algorithms based at least partly on an attribute of the health care claim;

determining that a first health care data record comprises a non-standard code representing a health care service not included in a list of coded health care services associated with the health care baseline algorithm;

determining a plurality of standard codes to collectively replace the non-standard code;

updating the first health care data record by replacing the non-standard code with the determined plurality of standard codes;

generating baseline data, representing a baseline amount for a health care service associated with the health care claim, using the one or more health care data records and the health care baseline algorithm;

generating display instructions for a graphical user interface comprising:
- a health care data overview portion that presents the baseline amount;
- a real-time adjustment detail portion that presents a result of adjusting health care data regarding the health care service in substantially real-time; and
- an interactive adjustment control, wherein a user interaction with the interactive adjustment control occurring after display of the health care data adjustment interface causes a change to an adjustment factor applied to the health care data, and wherein the real-time adjustment detail portion automatically updates, in response to the user interaction with the interactive adjustment control, presentation of:
  - a first result of adjusting the health care data using the changed adjustment factor; and
  - a second result of analyzing the baseline amount with respect to the first result; and sending the display instructions to the computing device.

11. The computer-implemented method of claim 10, wherein generating the display instructions for the graphical user interface further comprises generating display instructions to display the interactive adjustment control as a slider control, wherein a user interaction with the slider control causes a portion of the slider control to move toward a first limit and away from a second limit.

12. The computer-implemented method of claim 11, further comprising:
determining a value of the adjustment factor is based on a relative position of the portion of the slider control with respect to at least one of the first limit or the second limit.

13. The computer-implemented method of claim 10, wherein generating the display instructions for the graphical user interface further comprises generating display instructions to present, in the real-time adjustment detail portion, information regarding at least one of: a current value of the adjustment factor, a comparison of adjusted health care data to a baseline amount, or a comparison of adjusted health care data to costs incurred providing the health care service.

14. The computer-implemented method of claim 10, further comprising determining that a first health care service provider is likely to generate a health care claim including a value that is less than a value in a health care claim generated by a second health care service provider for the health care service, wherein the health care data adjustment interface further comprises an alternate provider section that presents information regarding the first health care service provider.

15. A system comprising:
computer-readable memory storing executable instructions; and one or more computer processors in communication with the computer-readable memory and configured by the executable instructions to at least:
receiving health data records associated with health care claims of a plurality of health care service providers, wherein a first health care data record is received in non-standard form dependent upon at least one of: a health care claim represented by the first health care data record, or a health care service provider from which the first health care data record originates;

generating health care baseline amounts for individual health care data records of the health care data records, wherein a first health care baseline amount is generated using the first health care data record and a health care baseline algorithm corresponding to the non-standard form of the first health care data record;

storing historical experience data representing processing health care data records with respect to historical experience based at least in part on (1) a degree to which individual health care service providers accept health care claim processing based at least in part on health care baseline amounts, or (2) acceptance status of customization of health care data associated with healthcare data records;

generate display instructions for a graphical user interface comprising:
- a map of a geographic area in which a first health care service provider is located;
- a first object representing a location of the first health care service provider within the geographic area, wherein a visual property of the first object represents a classification, of a plurality of predetermined claim valuation acceptance classifications, to which the first health care service provider is assigned based on historical experience processing health care data records associated with the first health care service provider, and wherein the historical experience processing health care data records is based on (1) a degree to which the first health care service provider accepts health care claim processing based at least in part on a plurality of health care baseline amounts, or (2) acceptance status of customization of health care data associated with the healthcare data records; and
- a second object representing a location of a second health care service provider within the geographic area, wherein a visual property of the second object represents a classification to which the second health care service provider is assigned based on historical experience processing health care data records associated with the second health care service provider; and send the display instructions to the computing device.

16. The system of claim 15, wherein the visual property of the first object comprises one of: a color of the first object, a texture of the first object, or a label assigned to the first object.

17. The system of claim 15, wherein the historical experience processing health care data records associated with the first health care service provider comprises experience processing disputed health care claims associated with the first health care service provider.

18. The system of claim 15, wherein the historical experience processing health care data records associated with the first health care service provider comprises comparing health care claims associated with the first health care service provider to at least one of: a baseline amount, or an amount of expenses incurred by the first health care service provider.

19. The system of claim 15, further configured to determine the classification to which the first health care service provider is assigned based at least partly on an analysis of health care data regarding a particular health care service provided by the first health care service provider.

20. The system of claim 15, further configured to determine the classification based at least partly on a predicted likelihood of the first health care service provider to dispute a health care claim associated with a particular health care service.

* * * * *

UNITED STATES PATENT AND TRADEMARK OFFICE
CERTIFICATE OF CORRECTION

PATENT NO. : 10,783,992 B1
APPLICATION NO. : 16/657762
DATED : September 22, 2020
INVENTOR(S) : Edward Day et al.

It is certified that error appears in the above-identified patent and that said Letters Patent is hereby corrected as shown below:

In the Specification

In Column 11, Line 29, delete "embodiments" and insert --embodiments.--.

In Column 24, Line 59, delete "("SDDs")," and insert --("SSDs"),--.

In the Claims

In Column 30, Line 36, delete "healthcare" and insert --health care--.

In Column 30, Line 57, delete "healthcare" and insert --health care--.

Signed and Sealed this
Tenth Day of May, 2022

Katherine Kelly Vidal
*Director of the United States Patent and Trademark Office*